US009933441B2

(12) United States Patent
Wu

(10) Patent No.: US 9,933,441 B2
(45) Date of Patent: *Apr. 3, 2018

(54) PROGRESSIVE APPROXIMATION OF SAMPLE ANALYTE CONCENTRATION

(71) Applicant: Bayer HealthCare LLC, Whippany, NJ (US)

(72) Inventor: Huan-Ping Wu, Granger, IN (US)

(73) Assignee: Ascensia Diabetes Care Holdings AG, Basel (CH)

( * ) Notice: Subject to any disclaimer, the term of this patent is extended or adjusted under 35 U.S.C. 154(b) by 226 days.

This patent is subject to a terminal disclaimer.

(21) Appl. No.: 14/775,070

(22) PCT Filed: Mar. 11, 2014

(86) PCT No.: PCT/US2014/023167
§ 371 (c)(1),
(2) Date: Sep. 11, 2015

(87) PCT Pub. No.: WO2014/159354
PCT Pub. Date: Oct. 2, 2014

(65) Prior Publication Data
US 2016/0033537 A1 Feb. 4, 2016

Related U.S. Application Data

(60) Provisional application No. 61/781,771, filed on Mar. 14, 2013.

(51) Int. Cl.
*G01N 33/48* (2006.01)
*G01N 33/50* (2006.01)
(Continued)

(52) U.S. Cl.
CPC ....... *G01N 33/723* (2013.01); *G01N 27/3274* (2013.01); *G06F 19/24* (2013.01)

(58) Field of Classification Search
None
See application file for complete search history.

(56) References Cited

U.S. PATENT DOCUMENTS 5,620,579 A 4/1997 Genshaw
5,653,863 A 8/1997 Genshaw
(Continued)

FOREIGN PATENT DOCUMENTS

CN 102116752 7/2011
EP 2 479 576 7/2012
(Continued)

OTHER PUBLICATIONS

English machine translation of CN 102116752 A obtained on Jun. 22, 2017.*

(Continued)

*Primary Examiner* — Russell S Negin
(74) *Attorney, Agent, or Firm* — Nixon Peabody LLP

(57) ABSTRACT

Error may be introduced into an analysis by both the biosensor system used to perform the analysis and by errors in the output signal measured by the measurement device of the biosensor. For a reference sample, system error may be determined through the determination of relative error. However, during an analysis of a test sample with the measurement device of the biosensor system, true relative error cannot be known. A pseudo-reference concentration determined during the analysis may be used as a substitute for true relative error. The closer the analysis-determined pseudo-reference analyte concentration is to the reference analyte concentration of the test sample, the more accurate and/or precise the analyte concentration determined by the measurement device using an anchor parameter during compensation. The present invention provides an improvement in the accuracy and/or precision of the analysis determined (Continued)

pseudo-reference concentration through progressive approximation.

20 Claims, 15 Drawing Sheets

(51) Int. Cl.
*G01N 33/72* (2006.01)
*G01N 27/327* (2006.01)
*G06F 19/24* (2011.01)

(56) References Cited

U.S. PATENT DOCUMENTS

| | | |
|---|---|---|
| 6,120,676 A | 9/2000 | Heller |
| 6,153,069 A | 11/2000 | Pottgen |
| 6,413,411 B1 | 7/2002 | Pottgen |
| 2009/0177406 A1 | 7/2009 | Wu |
| 2011/0231105 A1 | 9/2011 | Wu |
| 2013/0071869 A1 | 3/2013 | Wu |

FOREIGN PATENT DOCUMENTS

| | | |
|---|---|---|
| WO | WO 2007/013915 | 2/2007 |
| WO | WO 2007/040913 | 4/2007 |
| WO | WO 2009/108239 A2 * | 9/2009 |
| WO | WO 2010/077660 | 7/2010 |
| WO | WO 2012/125727 A1 * | 9/2012 |

OTHER PUBLICATIONS

Search Report for International Application No. PCT/US2014/023167 dated Jun. 8, 2014 (3 pages).
Written Opinion for International Application No. PCT/US2014/023167 dated Jun. 8, 2014 (6 pages).

* cited by examiner

100

- 110 — Measure at least two analyte responsive output signals, where the analyte responsive output signals are affected by at least one extraneous stimulus resulting from a physical characteristic, an environmental aspect, and/or a manufacturing variation error being incorporated into the analyte responsive output signal.

- 130 — Measure one or more extraneous stimulus responsive output signals from the reference samples and quantify the extraneous stimulus to provide at least two quantified extraneous stimulus values 132.

- 140 — Determine a normalizing relationship 142 from the analyte responsive output signals and the at least two quantified extraneous stimulus values 132 at a single selected sample analyte concentration.

- 150 — Determine a normalizing value 152 from the normalizing relationship 142 by inputting the quantified extraneous stimulus values 132 into the normalizing relationship 142.

- 160 — Divide the analyte responsive output signals by the normalizing values 152 to provide normalized analyte responsive output signals 162.

- 170 — Determine a normalized reference correlation 172 between the normalized analyte responsive output signals 162 and the reference sample analyte concentrations 114 by a regression technique.

FIG.1D

PROGRESSIVE APPROXIMATION OF SAMPLE ANALYTE CONCENTRATION

REFERENCE TO RELATED APPLICATIONS

This application is a U.S. national phase of International Application No. PCT/US2014/023167, filed Mar. 11, 2014, titled "Progressive Approximation of Sample Analyte Concentration," which claims the benefit of priority of U.S. Provisional Patent Application No. 61/781,771, filed Mar. 14, 2013, titled "Progressive Approximation of Sample Analyte Concentration," each of which are incorporated by reference in their entirety.

BACKGROUND

Biosensor systems provide an analysis of a biological fluid sample, such as blood, serum, plasma, urine, saliva, interstitial, or intracellular fluid. Typically, the systems include a measurement device that analyzes a sample residing in a test sensor. The sample usually is in liquid form and in addition to being a biological fluid, may be the derivative of a biological fluid, such as an extract, a dilution, a filtrate, or a reconstituted precipitate. The analysis performed by the biosensor system determines the presence and/or concentration of one or more analytes, such as alcohol, glucose, uric acid, lactate, cholesterol, bilirubin, free fatty acids, triglycerides, proteins, ketones, phenylalanine or enzymes, in the biological fluid. For example, a person with diabetes may use a biosensor system to determine the A1c or glucose level in blood for adjustments to diet and/or medication.

In blood samples including hemoglobin (Hb), the presence and/or concentration of total hemoglobin (THb) and glycated hemoglobin (HbA1c) may be determined. HbA1c (%-A1c) is a reflection of the state of glucose control in diabetic patients, providing insight into the average glucose control over the three months preceding the test. For diabetic individuals, an accurate measurement of %-A1c assists in determining how well the patient is controlling blood glucose levels with diet and/or medication over a longer term than provided by an instantaneous measure of blood glucose level. As an instantaneous blood glucose measurement does not indicate blood glucose control other than when the measurement is made.

Biosensor systems may be designed to analyze one or more analytes and may use different volumes of biological fluids. Some systems may analyze a single drop of blood, such as from 0.25-15 microliters (µL) in volume. Biosensor systems may be implemented using bench-top, portable, and like measurement devices. Portable measurement devices may be hand-held and allow for the identification and/or quantification of one or more analytes in a sample. Examples of portable measurement systems include the Contour® meters of Bayer HealthCare in Tarrytown, N.Y., while examples of bench-top measurement systems include the Electrochemical Workstation available from CH Instruments in Austin, Tex.

Biosensor systems may use optical and/or electrochemical methods to analyze the biological fluid. In some optical systems, the analyte concentration is determined by measuring light that has interacted with or been absorbed by a light-identifiable species, such as the analyte or a reaction or product formed from a chemical indicator reacting with the analyte. In other optical systems, a chemical indicator fluoresces or emits light in response to the analyte when illuminated by an excitation beam. The light may be converted into an electrical output signal, such as current or potential, which may be similarly processed to the output signal from an electrochemical system. In either optical system, the system measures and correlates the light with the analyte concentration of the sample.

In light-absorption optical systems, the chemical indicator produces a reaction product that absorbs light. A chemical indicator such as tetrazolium along with an enzyme such as diaphorase may be used. Tetrazolium usually forms formazan (a chromagen) in response to the redox reaction of the analyte. An incident input beam from a light source is directed toward the sample. The light source may be a laser, a light emitting diode, or the like. The incident beam may have a wavelength selected for absorption by the reaction product. As the incident beam passes through the sample, the reaction product absorbs a portion of the incident beam, thus attenuating or reducing the intensity of the incident beam. The incident beam may be reflected back from or transmitted through the sample to a detector. The detector collects and measures the attenuated incident beam (output signal). The amount of light attenuated by the reaction product is an indication of the analyte concentration in the sample.

In light-generated optical systems, the chemical indicator fluoresces or emits light in response to the analyte redox reaction. A detector collects and measures the generated light (output signal). The amount of light produced by the chemical indicator is an indication of the analyte concentration in the sample and is represented as a current or potential from the detector.

An example of an optical system using reflectance is a laminar flow %-A1c system that determines the concentration of A1c hemoglobin in blood. These systems use immunoassay chemistry where the blood is introduced to the test sensor of the biosensor system where it reacts with reagents and then flows along a reagent membrane. When contacted by the blood, A1c antibody coated color beads release and move along with the blood to a detection Zone 1. Because of the competition between the A1c in the blood sample and an A1c peptide present in detection Zone 1 for the color beads, color beads not attached to the A1c antibody are captured at Zone 1 and are thus detected as the A1c signal from the change in reflectance. The total hemoglobin (THb) in the blood sample also is reacting with other blood treatment reagents and moves downstream into detection Zone 2, where it is measured at a different wavelength. For determining the concentration of A1c in the blood sample, the reflectance signal is proportional to the A1c analyte concentration (%-A1c), but is affected by the THb content of the blood. For the THb measurement, however, the reflectance in Zone 2 is inversely proportional to the THb (mg/mL) of the blood sample, but is not appreciably affected by the A1c content of the blood.

In electrochemical systems, the analyte concentration of the sample is determined from an electrical signal generated by an oxidation/reduction or redox reaction of the analyte or a measurable species responsive to the analyte concentration when an input signal is applied to the sample. The input signal may be a potential or current and may be constant, variable, or a combination thereof such as when an AC signal is applied with a DC signal offset. The input signal may be applied as a single pulse or in multiple pulses, sequences, or cycles. An enzyme or similar species may be added to the sample to enhance the electron transfer from the analyte during the redox reaction. The enzyme or similar species may react with a single analyte, thus providing specificity to a portion of the generated output signal. A redox mediator may be used as the measurable species to maintain the oxidation state of the enzyme and/or assist with electron transfer from the analyte to an electrode. Thus, during the redox reaction, an enzyme or similar species may transfer electrons between the analyte and the redox mediator, while the redox mediator transfers electrons between itself and an electrode of the test sensor.

Electrochemical biosensor systems usually include a measurement device having electrical contacts that connect with the electrical conductors of the test sensor. The conductors may be made from conductive materials, such as solid metals, metal pastes, conductive carbon, conductive carbon pastes, conductive polymers, and the like. The electrical conductors connect to working and counter electrodes, and may connect to reference and/or other electrodes that extend into a sample reservoir depending on the design of the test sensor. One or more electrical conductors also may extend into the sample reservoir to provide functionality not provided by the electrodes.

In many biosensor systems, the test sensor may be adapted for use outside, inside, or partially inside a living organism. When used outside a living organism, a sample of the biological fluid may be introduced into a sample reservoir in the test sensor. The test sensor may be placed in the measurement device before, after, or during the introduction of the sample for analysis. When inside or partially inside a living organism, the test sensor may be continually immersed in the sample or the sample may be intermittently introduced to the test sensor. The test sensor may include a reservoir that partially isolates a volume of the sample or be open to the sample. When open, the test sensor may take the form of a fiber or other structure placed in contact with the biological fluid. Similarly, the sample may continuously flow through the test sensor, such as for continuous monitoring, or be interrupted, such as for intermittent monitoring, for analysis.

The measurement device of an electrochemical biosensor system applies an input signal through the electrical contacts to the electrical conductors of the test sensor. The electrical conductors convey the input signal through the electrodes into the sample present in the sample reservoir. The redox reaction of the analyte generates an electrical output signal in response to the input signal. The electrical output signal from the test sensor may be a current (as generated by amperometry or voltammetry), a potential (as generated by potentiometry/galvanometry), or an accumulated charge (as generated by coulometry). The measurement device may have the processing capability to measure and correlate the output signal with the presence and/or concentration of one or more analytes in the sample.

In coulometry, a potential is applied to the sample to exhaustively oxidize or reduce the analyte. A biosensor system using coulometry is described in U.S. Pat. No. 6,120,676. In amperometry, an electric signal of constant potential (voltage) is applied to the electrical conductors of the test sensor while the measured output signal is a current. Biosensor systems using amperometry are described in U.S. Pat. Nos. 5,620,579; 5,653,863; 6,153,069; and 6,413,411. In voltammetry, an electric signal of varying potential is applied to a sample of biological fluid, while the measured output is current. In gated amperometry and gated voltammetry, pulsed inputs are used as described in WO 2007/013915 and WO 2007/040913, respectively.

Primary output signals are responsive to the analyte concentration of the sample and are obtained from an analytic input signal. Output signals that are substantially independent of signals responsive to the analyte concentration of the sample include signals responsive to temperature and signals substantially responsive to interferents, such as the hematocrit or acetaminophen content of a blood sample when the analyte is glucose, for example. Output signals substantially not responsive to analyte concentration may be referred to as secondary output signals, as they are not primary output signals responsive to the alteration of light by the analyte or analyte responsive indicator, the electrochemical redox reaction of the analyte, or the electrochemical redox reaction of the analyte responsive redox mediator. Secondary output signals are responsive to the physical or environmental characteristics of the biological sample. Secondary output signals may arise from the sample or from other sources, such as a thermocouple that provides an estimate of an environmental characteristic of the sample. Thus, secondary output signals may be determined from the analytic input signal or from another input signal.

When arising from the sample, secondary output signals may be determined from the electrodes used to determine the analyte concentration of the sample, or from additional electrodes. Additional electrodes may include the same reagent composition as the electrodes used to determine the analyte concentration of the sample, a different reagent composition, or no reagent composition. For example, a reagent composition may be used that reacts with an interferent or an electrode lacking reagent composition may be used to study one or more physical characteristics of the sample, such as whole blood hematocrit.

The measurement performance of a biosensor system is defined in terms of accuracy and precision. Accuracy reflects the combined effects of systematic and random error components. Systematic error, or trueness, is the difference between the average value determined from the biosensor system and one or more accepted reference values for the analyte concentration of the biological fluid. Trueness may be expressed in terms of mean bias, with larger mean bias values representing lower trueness and thereby contributing to less accuracy. Precision is the closeness of agreement among multiple analyte readings in relation to a mean. One or more error in the analysis contributes to the bias and/or imprecision of the analyte concentration determined by the biosensor system. A reduction in the analysis error of a biosensor system therefore leads to an increase in accuracy and/or precision and thus an improvement in measurement performance.

Bias may be expressed in terms of "absolute bias" or "percent bias". Absolute bias is the difference between the determined concentration and the reference concentration, and may be expressed in the units of the measurement, such as mg/dL, while percent bias may be expressed as a percentage of the absolute bias value over the reference concentration, or expressed as a percentage of the absolute bias over either the cut-off concentration value or the reference concentration of the sample. For example, if the cut-off concentration value is 100 mg/dL, then for glucose concentrations less than 100 mg/dL, percent bias is defined as (the absolute bias over 100 mg/dL)*100; for glucose concentrations of 100 mg/dL and higher, percent bias is defined as the absolute bias over the accepted reference value of analyte concentration*100.

Accepted reference values for the analyte glucose in blood samples are preferably obtained with a reference instrument, such as the YSI 2300 STAT PLUS™ available from YSI Inc., Yellow Springs, Ohio. Other reference instruments and ways to determine percent bias may be used for other analytes. For the %-A1c measurements, the error may be expressed as either absolute bias or percent bias against the %-A1c reference value for the therapeutic range of 4-12%. Accepted reference values for the %-A1c in blood samples may be obtained with a reference instrument, such as the Tosoh G7 instrument available from Tosoh Corp, Japan.

Biosensor systems may provide an output signal during the analysis of the biological fluid including error from multiple error sources. These error sources contribute to the total error, which may be reflected in an abnormal output signal, such as when one or more portions or the entire output signal is non-responsive or improperly responsive to the analyte concentration of the sample.

The total error in the output signal may originate from one or more error contributors, such as the physical characteristics of the sample, the environmental aspects of the sample, the operating conditions of the system, the manufacturing variation between test sensor lots, and the like. Physical characteristics of the sample include hematocrit (red blood cell) concentration, interfering substances, such as lipids and proteins, and the like. Interfering substances for glucose analyses also may include ascorbic acid, uric acid, acetaminophen, and the like. Environmental aspects of the sample include temperature, oxygen content of the air, and the like. Operating conditions of the system include underfill conditions when the sample size is not large enough, slow-filling of the test sensor by the sample, intermittent electrical contact between the sample and one or more electrodes of the test sensor, degradation of the reagents that interact with the analyte after the test sensor was manufactured, and the like. Manufacturing variations between test sensor lots include changes in the amount and/or activity of the reagents, changes in the electrode area and/or spacing, changes in the electrical conductivity of the conductors and electrodes, and the like. A test sensor lot is preferably made in a single manufacturing run where lot-to-lot manufacturing variation is substantially reduced or eliminated. There may be other contributors or a combination of error contributors that cause error in the analysis.

Percent bias, mean percent bias, percent bias standard deviation (SD), percent coefficient of variance (%-CV), and hematocrit sensitivity are independent ways to express the measurement performance of a biosensor system. Additional ways may be used to express the measurement performance of a biosensor system.

Percent bias is a representation of the accuracy of the biosensor system in relation to a reference analyte concentration, while the percent bias standard deviation reflects the accuracy of multiple analyses, with regard to error arising from the physical characteristics of the sample, the environmental aspects of the sample, the operating conditions of the system, and the manufacturing variations between test sensors. Thus, a decrease in percent bias standard deviation represents an increase in the measurement performance of the biosensor system across multiple analyses. The percent coefficient of variance may be expressed as 100%*(SD of a set of samples)/(the average of multiple readings taken from the same set of samples) and reflects precision of multiple analyses. Thus, a decrease in percent bias standard deviation represents an increase in the measurement performance of the biosensor system across multiple analyses.

The mean may be determined for the percent biases determined from multiple analyses using test sensors from a single lot to provide a "mean percent bias" for the multiple analyses. The mean percent bias may be determined for a single lot of test sensors by using a subset of the lot, such as 80-140 test sensors, to analyze multiple blood samples.

Relative error is a general expression of error that may be expressed as $\Delta A / A_{ref}$ (relative error)=$(A_{calculated} - A_{ref})/A_{ref} = A_{calculated}/A_{ref} - 1$; where $\Delta A$ is the error present in the analysis determined analyte concentration in relation to the reference analyte concentration; $A_{calculated}$ is the analyte concentration determined from the sample during the analysis with a measurement device; and $A_{ref}$ is the reference analyte concentration of the sample.

Increasing the measurement performance of the biosensor system by reducing error from these or other sources means that more of the analyte concentrations determined by the biosensor system may be used for accurate therapy by the patient when blood glucose is being monitored, for example. Additionally, the need to discard test sensors and repeat the analysis by the patient also may be reduced.

Biosensor systems may have a single source of uncompensated output signals responsive to a redox or light-based reaction of the analyte, such as the counter and working electrodes of an electrochemical system. Biosensor systems also may have more than one source of uncompensated output responsive or non-responsive to the analyte concentration of the sample. For example, in an A1c biosensor, there may be one or more output signals responsive to the analyte concentration of the sample, but there also may be one or more output signals responsive to total hemoglobin (THb) that is not responsive to the analyte concentration of the sample, but which affect the analyte responsive signal/s.

Many biosensor systems include one or more methods to compensate for error associated with an analysis, thus attempting to improve the measurement performance of the biosensor system. Compensation methods may increase the measurement performance of a biosensor system by providing the biosensor system with the ability to compensate for inaccurate analyses, thus increasing the accuracy and/or precision of the concentration values obtained from the system. However, these methods have had difficulty compensating the errors in the analysis attributable to errors introduced by the biosensor system itself (system error) and errors originating from the analysis (output signal error). The present invention avoids or ameliorates at least some of the disadvantages of analyte concentration determination systems that did not compensate for both system and output signal errors.

SUMMARY

In one aspect, the invention provides a method for determining an analyte concentration in a sample that includes generating at least two output signals from a sample; measuring at least two analyte responsive output signals from the sample; determining at least two initial analyte concentrations from the at least two analyte responsive output signals; determining a first pseudo-reference concentration from the at least two analyte responsive output signals, where the first pseudo-reference concentration is a first substitute for true relative error; determining at least one first anchor parameter in response to the first pseudo-reference concentration, where the at least one first anchor parameter compensates for system error; incorporating the at least one first anchor parameter into at least two first compensation relationships; determining at least two first anchor compensated analyte concentrations in response to the at least two initial analyte concentrations, the at least two first anchor parameters, and the at least two first compensation relationships; determining a second pseudo-reference concentration by averaging the at least two first anchor compensated analyte concentrations, where the second pseudo-reference concentration is a second substitute for true relative error; and reporting the second pseudo-reference concentration as a final compensated analyte concentration of the sample.

In another aspect of the invention, there is an analyte measurement device that includes electrical circuitry connected to a sensor interface, where the electrical circuitry includes a processor connected to a signal generator and a storage medium; where the processor is capable of measuring at least two analyte responsive output signals from the sample; where the processor is capable of determining at least two initial analyte concentrations from the at least two analyte responsive output signals; where the processor is capable of determining a first pseudo-reference concentration from the at least two analyte responsive output signals, where the first pseudo-reference concentration is a first substitute for true relative error; where the processor is capable of determining at least one first anchor parameter in response to the first pseudo-reference concentration, where the at least one first anchor parameter compensates for system error; where the processor is capable of incorporating the at least one first anchor parameter into at least two first compensation relationships; where the processor is capable of determining at least two first anchor compensated analyte concentrations in response to the at least two initial analyte concentrations, the at least two first anchor parameters, and the at least two first compensation relationships; where the processor is capable of determining a second pseudo-reference concentration by averaging the at least two first anchor compensated analyte concentrations, where the second pseudo-reference concentration is a second substitute for true relative error; and where the processor is capable of reporting the second pseudo-reference concentration as a final compensated analyte concentration of the sample.

In another aspect of the invention, there is a biosensor system for determining an analyte concentration in a sample that includes a test sensor having a sample interface adjacent to a reservoir formed by a base, where the test sensor is capable of generating at least two output signals from a sample; and a measurement device having a processor connected to a sensor interface, the sensor interface having electrical communication with the sample interface, and the processor having electrical communication with a storage medium; where the processor is capable of measuring at least two analyte responsive output signals from the sample; where the processor is capable of determining at least two initial analyte concentrations from the at least two analyte responsive output signals; where the processor is capable of determining a first pseudo-reference concentration from the at least two analyte responsive output signals, where the first pseudo-reference concentration is a first substitute for true relative error; where the processor is capable of determining at least one first anchor parameter in response to the first pseudo-reference concentration, where the at least one first anchor parameter compensates for system error; where the processor is capable of incorporating the at least one first anchor parameter into at least two first compensation relationships; where the processor is capable of determining at least two first anchor compensated analyte concentrations in response to the at least two initial analyte concentrations, the at least two first anchor parameters, and the at least two first compensation relationships; where the processor is capable of determining a second pseudo-reference concentration by averaging the at least two first anchor compensated analyte concentrations, where the second pseudo-reference concentration is a second substitute for true relative error; and where the processor is capable of reporting the second pseudo-reference concentration as a final compensated analyte concentration of the sample.

BRIEF DESCRIPTION OF THE DRAWINGS

The invention can be better understood with reference to the following drawings and description. The components in the figures are not necessarily to scale, emphasis instead being placed upon illustrating the principles of the invention.

FIG. 1D represents a factory calibration method of determining calibration information through a normalization procedure.

FIG. 1D-1 shows the individual A1c reflectance signals recorded from the Zone 1 detector/s of the measurement device separated for the four different THb concentrations in blood samples.

FIG. 1D-2 represents the determined normalized reference correlation 172 expressed as a normalized calibration curve.

FIG. 1E-1 provides an example of the determination of a second normalizing relationship in a glucose analysis system.

FIG. 1E-2 provides an example of determining second normalized analyte responsive output signals in a glucose analysis system.

FIG. 1E-3 provides an example of determining a second normalized reference correlation in a glucose analysis system.

FIG. 3 depicts a schematic representation of a biosensor system 300 that determines an analyte concentration in a sample of a biological fluid.

DETAILED DESCRIPTION

Figure 1A:
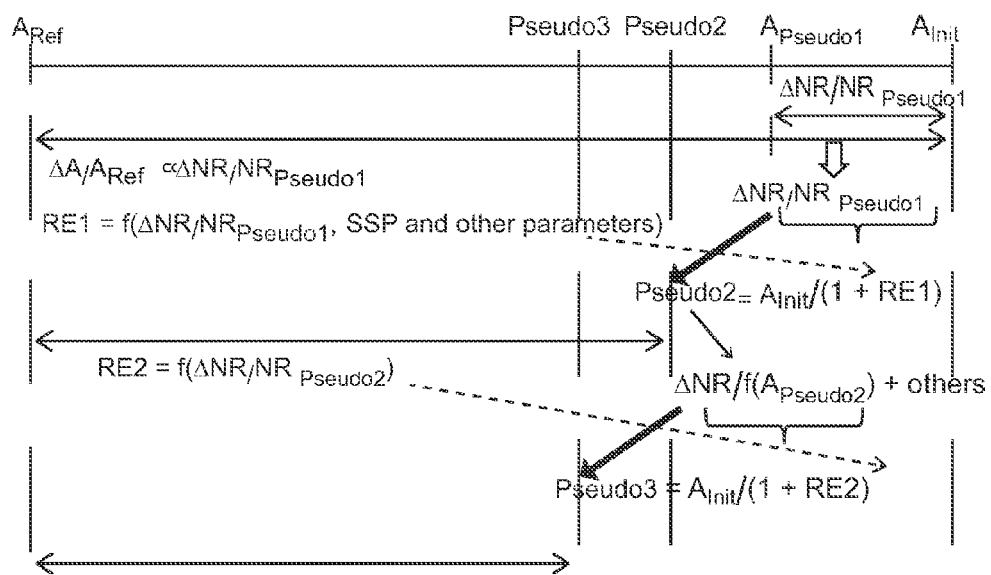
FIG. 1A is a pictorial representation of this progressive approximation, where reference or "true" analyte concentration of the sample ($A_{Ref}$) is on the far left and the initially determined analyte concentration from the measurement device ($A_{Init}$) is on the far right.

During analyte analysis, errors may be introduced into the analysis by both the biosensor system used to perform the analysis and by errors in the output signal measured by the measurement device of the biosensor. Biosensor system errors may occur from multiple sources, with an error source being in the reference correlation stored in the measurement device of the biosensor system. Thus, the laboratory determined calibration information used to convert the output signals measured by the measurement device during an analysis of a test sample into the determined analyte concentration of the sample includes error.

While one might expect system errors introduced by the calibration information of the measurement device to be the same for every analysis, and thus straightforward to remove before the measurement device is used, this is not correct for all types of system errors. Some errors in the calibration information only arise under the conditions of a specific analysis, and thus cannot be removed from the calibration information without a change that would result in a system error for another specific analysis. Thus, it is difficult to reduce system error for the conditions of one specific analysis without potentially adversely affecting the system error for a different specific analysis when system error arises from the calibration information. The output signal errors arise from one or more error contributors, such as the physical characteristics of the sample, the environmental aspects of the sample, the operating conditions of the system, and the manufacturing variation between test sensor lots. These output signal errors may become amplified or complicated when the signal is converted to a concentration by the calibration information.

For a reference sample, system error may be determined through the determination of relative error by subtracting the reference sample analyte concentration from the measurement device determined analyte concentration and dividing by the reference sample analyte concentration ($A_{calc}-A_{ref}/A_{ref}$). The reference sample analyte concentration of the reference samples may be determined using a reference instrument, by mixing or altering known sample analyte concentrations, and the like.

However, during an analysis of a test sample with the measurement device of the biosensor system, the reference sample analyte concentration is not known. Instead, the biosensor system performs the analysis to determine the analyte concentration in the sample to the according to the design and implementation of the measurement device. Thus, "true relative error" cannot be determined by the measurement device during an analysis as the true concentration of the analyte in the sample is not known.

A pseudo-reference concentration determined during the analysis by the measurement device may be used as a substitute for true relative error. From the analysis-determined pseudo-reference concentration, an anchor parameter may be determined and used to compensate for the system error in the analysis-determined pseudo-reference concentration. However, the closer the analysis-determined pseudo-reference analyte concentration is to the reference analyte concentration of the test sample, the more accurate and/or precise the analyte concentration determined by the measurement device using an anchor parameter during compensation. The present invention provides an improvement in the accuracy and/or precision of the analysis determined pseudo-reference concentration through progressive approximation.

The described methods, devices, and systems may provide an improvement in measurement performance by considering both system and output signal errors when determining the final analyte concentration of the sample through the use of an anchor parameter determined with a progressively approximated pseudo-reference concentration. Both system and signal errors may be "linked" in the compensation used to determine the final analyte concentration of the sample when a signal-based anchor parameter is used. Preferably, both system and output signal errors are considered by the compensation used to determine the final analyte concentration of the sample.

The measurement of %-A1c in blood samples, thus the concentration of glycated hemoglobin (%-A1c) in the total hemoglobin (THb) content of a blood sample, may be accomplished by an immunoassay method using a laminar flow analysis. Conventionally, in the laminar flow analysis two independent signals are measured, primary output signals for the A1c and secondary output signals for the THb. In this type of A1c system, the Zone 1 detectors provide the primary output signal while the Zone 2 detectors provide the secondary output signal. The primary output signals from the Zone 1 detector/s depend on the A1c concentration of the sample, but also on the THb concentration of the sample. The secondary output signals from the Zone 2 detector/s depend on the THb concentration of the sample, but are substantially independent of the A1c concentration of the sample. The secondary output signals measured during the analysis by the measurement device are responsive to an extraneous stimulus. In a %-A1c analysis biosensor system, the analyte is A1c and extraneous stimuli are temperature and the THb.

While a single sample is applied to the test sensor, the described %-A1c analysis system has two channels that perform two independent analyses of the sample. Thus, for the first analysis, the Zone 1 Channel1 (Ch1) detector and the Zone 2 Channel 2 (Ch2) detector provide the primary and secondary output signals, respectively. For the second analysis, the Zone 1 Channel 3 (Ch3) detector and the Zone 2 Channel 4 (Ch4) detector provide the primary and secondary output signals, respectively. As the sample is analyzed twice using the same general method, the concentration determined for the first analysis may be averaged with the concentration determined for the second analysis. Also, the different Ch1/Ch2 and Ch3/Ch4 signals may be averaged or otherwise manipulated at the signal level for compensation.

For a %-A1c analysis measurement device having two primary output signal channels from the Zone 1 Ch1 and Ch3 detectors, the laboratory determined relative error in Ch1 may be expressed as Ch1 Relative Error=$(A_{Init}-A_{Ref})/A_{Ref}$ or $dA1/A_{Ref}$, where $A_{Init}$ is the %-A1c concentration of the reference sample as determined by the measurement device of the biosensor system and $A_{Ref}$ is the known analyte concentration of the reference sample. The relative error for Ch3 of the measurement device may be similarly determined and expressed as $dA3/A_{Ref}$.

As this relative error cannot be determined during a test sample analysis with the measurement device of the biosensor system, a pseudo-reference concentration is determined as a substitute for relative error. Progressive approximation is used to move the concentration determined for the pseudo-reference closer to the actual analyte concentration of the test sample should be.

FIG. 1A is a pictorial representation of this progressive approximation, where reference or "true" analyte concentration of the sample ($A_{Ref}$) is on the far left and the initially determined analyte concentration from the measurement device ($A_{Init}$) is on the far right. The measurement device determined pseudo-reference concentration starts closer to $A_{Init}$ than to $A_{Ref}$, but is moved closer to $A_{Ref}$ by the progressive approximation of the present invention. After an initial and an anchor parameter compensated analyte concentration using a first pseudo-reference concentration is determined for channels Ch1 and Ch3, an average of the Ch1 and Ch3 concentrations is determined and used as a second pseudo-reference concentration. A second anchor parameter is determined from this second pseudo-reference concentration and a third pseudo-reference concentration determined by compensating the initial concentration using the second anchor parameter from the second pseudo-reference concentration. The third pseudo-reference could then be used to determine a third anchor parameter and a fourth pseudo-reference concentration determined. Additional pseudo-reference concentrations and corresponding anchor parameters determined to continue the progressive approximation of pseudo-reference concentrations.

After some number of pseudo-reference concentrations are determined, a point of diminishing returns is reached. Depending on the improvement in compensation being obtained from each determined anchor parameter, the progressive approximations may be stopped and the selected pseudo-reference concentration reported as the compensated final analyte concentration of the sample. Each progressively determined anchor parameter preferably has a better correlation with the system error in the pseudo-reference concentration. Thus, when an anchor parameter determined from a pseudo-reference concentration can no longer remove sufficient system error in view of the measurement performance requirements of the biosensor system, the progressive approximation may be stopped. The second, third, or later determined pseudo-reference concentration may be reported as the compensated final analyte concentration of the sample.

Figure 1B:
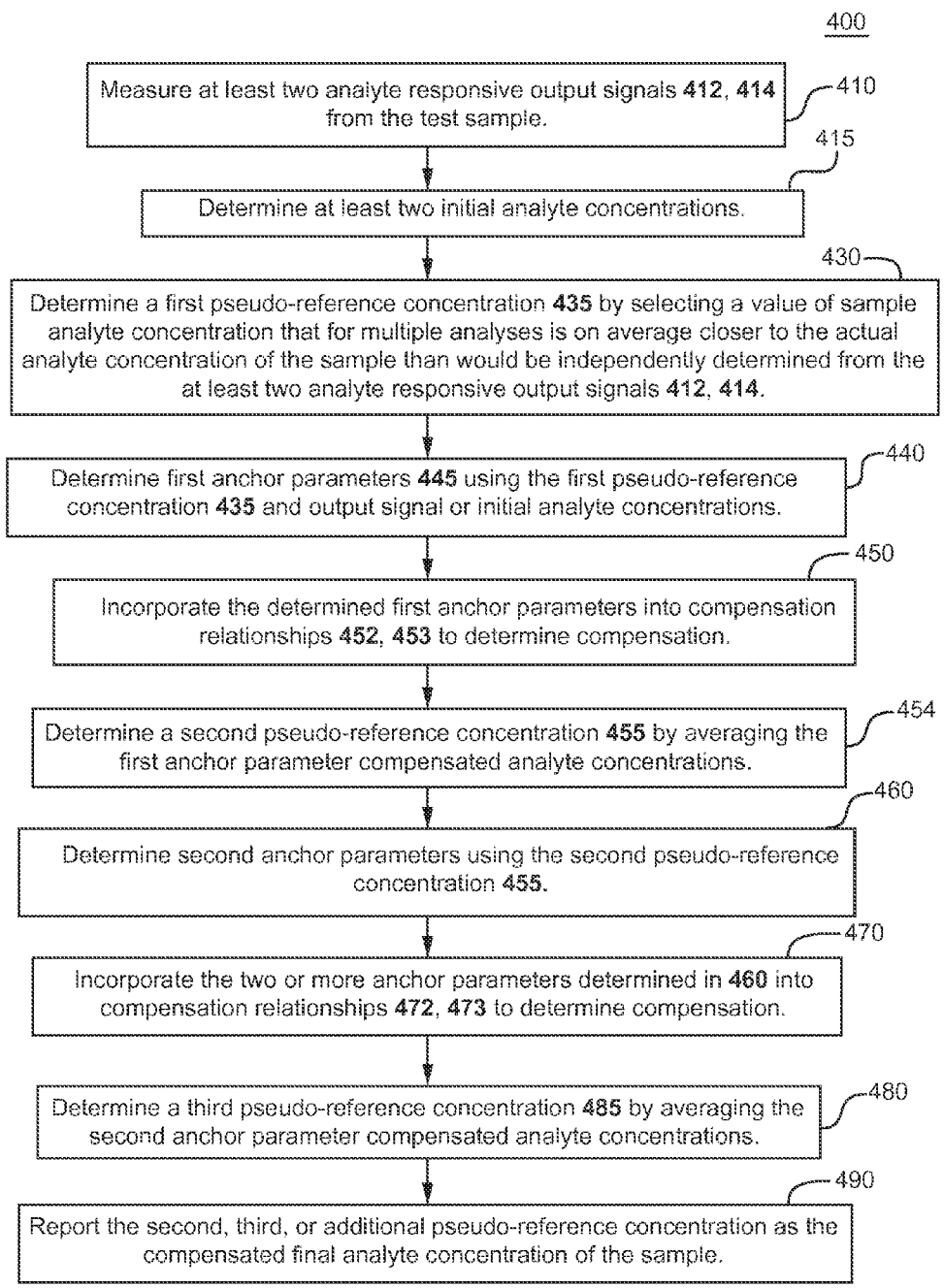
FIG. 1B represents an analysis method as would be implemented in the measurement device of a biosensor system.

FIG. 1B represents an analysis method 400 as would be implemented in the measurement device of a biosensor system. The compensation of the method 400 uses an anchor parameter determined through the progressive approximation of pseudo-reference concentrations to compensate for system error in the final compensated analyte concentration of a sample. The method 400 may be used in any biosensor system where at least two analyte concentrations may be determined for the same test sample. The at least one anchor parameter may be used in a method of error compensation where the conversion relationship internalizes the reduction of error arising from major error contributors, where the error from the major error contributors is reduced through primary compensation distinct from the conversion relationship, where residual compensation is used with the conversion relationship, or where the residual compensation is used with the primary compensation and the conversion relationship. The major error contributors for %-A1c analyses are temperature and total hemoglobin, while in glucose analyses the major error contributors are temperature and hematocrit. The major error contributors may be different for different types of analyte analysis.

In analysis output signal measurement 410, at least two analyte responsive output signals 412, 414 are measured from the test sample with the measurement device of the biosensor system. The at least two analyte responsive output signals 412, 414 preferably are independent analyte responsive output signals such as output signals generated from separate portions of the sample, the independent output signals from multi-zone detectors, and the like. In a %-A1c biosensor system, the at least two analyte responsive output signals 412, 414 are independent in that they are measured from different portions of the test sample by different detector channels. The at least two analyte responsive output signals are generated from a sample of a biological fluid in response to a light-identifiable species or an oxidation/reduction (redox) reaction of the analyte. Depending on the biosensor system, these primary output signals may or may not include the effect of an extraneous stimulus.

Figure 1C:
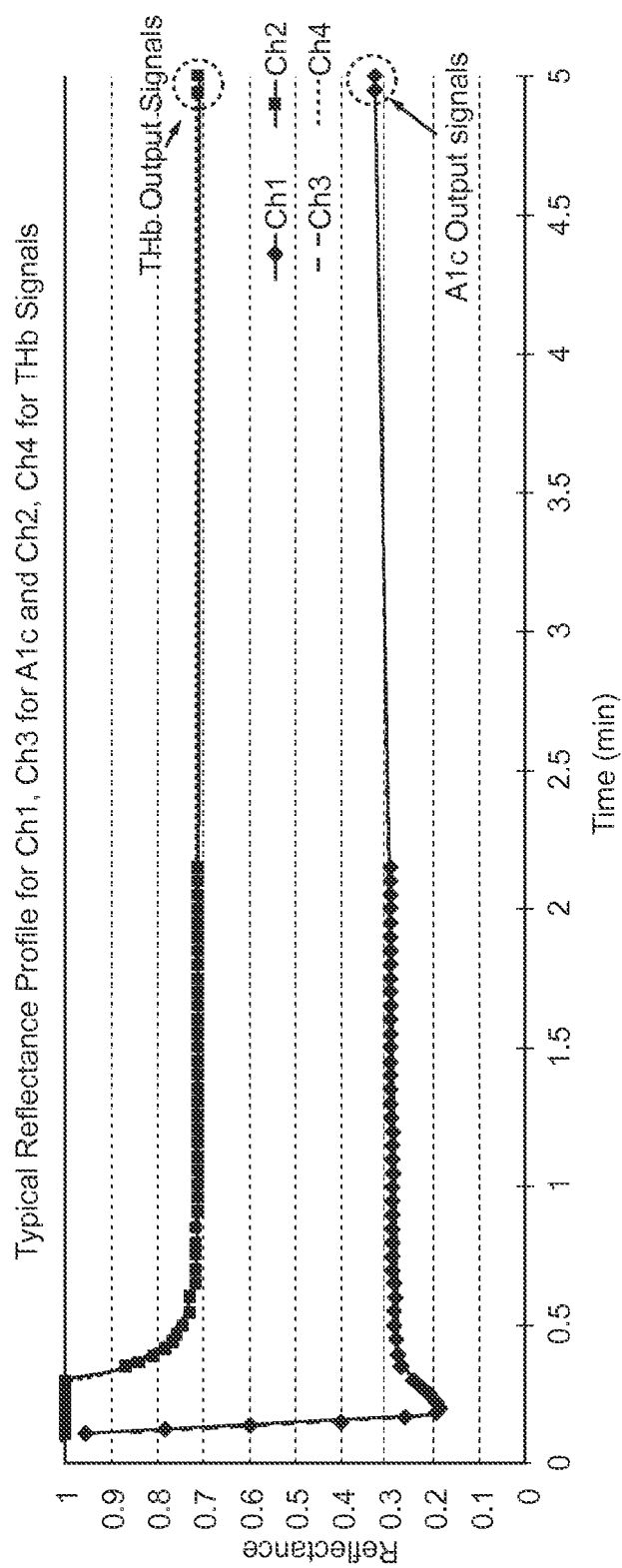
FIG. 1C depicts the output signals recorded from the four output channels of an A1c analysis biosensor system.

FIG. 1C depicts the output signals recorded from the four output channels of an A1c analysis biosensor system. The independent signals from the two Zone 1 detectors (Ch1 and Ch3 detectors) depend on the A1c concentration of the sample, but also on the THb content of the sample. The independent signals from the two Zone 2 detectors (Ch2 and Ch4 detectors) are independent of the A1c concentration of the sample, but depend on the THb concentration of the sample. The figure shows the outputs for Ch1 and Ch2. In this type of A1c system, the Zone 1 detectors provide the primary output signals while the Zone 2 detectors provide the secondary output signals. The analyte responsive (e.g. A1c) primary output signals and extraneous stimulus (e.g. THb) responsive secondary output signals may be used in the analysis analyte responsive output signal measurement 410.

In analysis initial analyte concentration determination 415, at least two initial analyte concentrations are determined for the test sample. The at least two analyte responsive output signals 412, 414 (primary output signals) are used to determine an initial analyte concentration for each signal. The same or different methods may be used to determine the initial analyte concentration for each of the at least two analyte responsive output signals 412, 414. The calibration information used by the measurement device to determine the at least two initial analyte concentrations may or may not provide a reduction in the effect of one or more extraneous stimulus on the primary output signals, such as through the use of normalized calibration information. Thus, the initial analyte concentrations may be determined with calibration information including a conventional reference correlation and output signals as measured by the measurement device lacking a reduction in extraneous stimulus effect, a normalized reference correlation and normalized output signals providing a reduction in extraneous stimulus effect, or either type of calibration information in combination with primary compensation providing a reduction in extraneous stimulus effect. Calibration information including the normalizing relationship and the normalized reference correlation is further discussed with regard to FIG. 1D and FIG. 1E.

Primary compensation internalized in a conversion relationship may be algebraic in nature, thus linear or non-linear algebraic equations may be used to express the relationship between the determined analyte concentration of the sample and the uncompensated output signal and error parameters. For example, in a %-A1c biosensor system, temperature (T) and total hemoglobin (THb) are the major error contributors. Similarly to hematocrit error in blood glucose analysis, different total hemoglobin contents of blood samples can result in different A1c signals erroneously leading to different A1c concentrations being determined for the same underlying A1c concentration. Thus, an algebraic equation to compensate these errors may be $A1c = a_1 * S_{A1c} + a_2/S_{A1c} + a_3 * THb + a_4 * THb^2$, where A1c is the analyte concentration after conversion of the uncompensated output values and primary compensation for total hemoglobin, $S_{A1c}$ is the temperature compensated output values (e.g. reflectance or adsorption) representing A1c, and THb is the total hemoglobin value calculated by $THb=d_0+d_1/S_{THb}+d_2/S_{THb}^2+d_3/S_{THb}^3$, where $S_{THb}$ is the temperature corrected THb reflectance signal obtained from the test sensor. The temperature effects for $S_{A1c}$ and $S_{THb}$ may be corrected with the algebraic relationship $S_{A1c}=S_{A1c}(T)+[b_0+b_1*(T-T_{ref})+b_2*(T-T_{ref})^2]$ and $S_{THb}=[S_{THb}(T)c_0+c_1*(T-T_{ref})]/[c_2*(T-T_{ref})^2]$. By algebraic substitution, the primary compensated analyte concentration A may be calculated with conversion of the uncompensated output values and primary compensation for the major error contributors of temperature and total hemoglobin being integrated into a single algebraic equation. More detail regarding primary compensation also may be found in U.S. Pat. Pub. 2011/0231105, entitled "Residual Compensation Including Underfill Error", filed Mar. 22, 2011 or in U.S. Pat. Pub. 2013/0071869, entitled "Analysis Compensation Including Segmented Signals", filed Sep. 20, 2012.

In analysis first pseudo-reference concentration determination 430, a first pseudo-reference concentration 435 is determined. The first pseudo-reference concentration 435 is determined by determining a sample analyte concentration that for multiple analyses is on average closer to the actual analyte concentration of the sample than would be determined from either of the at least two analyte responsive output signals 412, 414. Thus, the pseudo-reference is an approximation of the analyte concentration of the sample that is closer to the reference concentration on average than a concentration determined from an individual primary output signal of the measurement device.

The first pseudo-reference concentration 435 may be determined by averaging the two or more initial analyte concentrations. The first pseudo-reference concentration 435 also may be determined by averaging the at least two independent analyte responsive output signals 412, 414 and then determining the first pseudo-reference concentration 435 from the averaged signal. In this instance, the actual determination of the at least two initial analyte sample concentrations is not required for determination of the first pseudo-reference concentration, as the primary output signals may be averaged and used to determine the pseudo-reference concentration 435 as opposed to determined concentrations. The method of determining the first pseudo-reference concentration 435 and any associated relationships is preferably pre-determined in the laboratory and stored in the storage medium of the measurement device of the biosensor system for use during the analysis of the test sample.

In analysis first anchor parameter value determination 440, an anchor parameter is determined for the at least two channels using the first pseudo-reference concentration 435 and the at least two analyte responsive output signals 412, 414 or the initial analyte concentrations determined from the at least two primary output signals. A signal-based anchor parameter is determined for the at least two channels using the first pseudo-reference concentration 435 and the at least two analyte responsive output signals 412, 414. A concentration-based anchor parameter is determined for the at least two channels using the first pseudo-reference concentration 435 and the initial analyte concentrations determined from the at least two analyte responsive output signals 412, 414.

Figures 1, 1D:
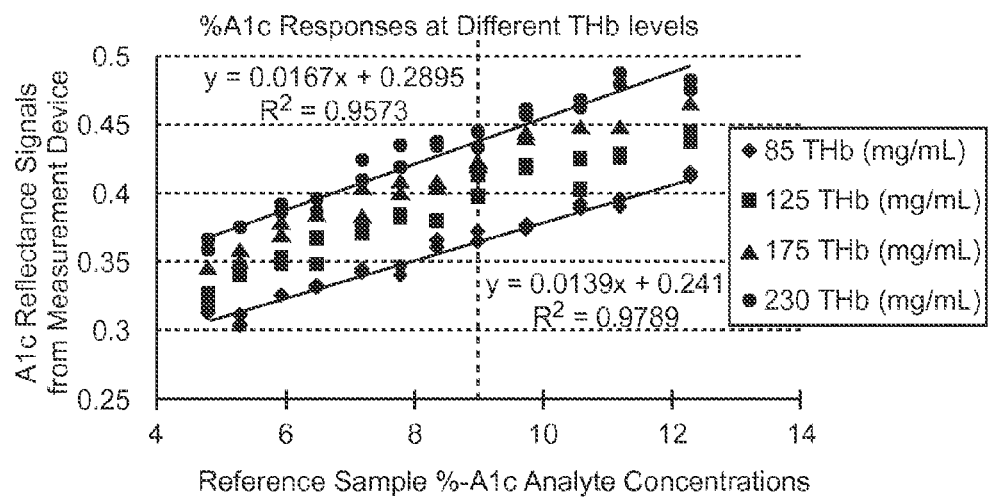
Figures 1, 1D, 2:
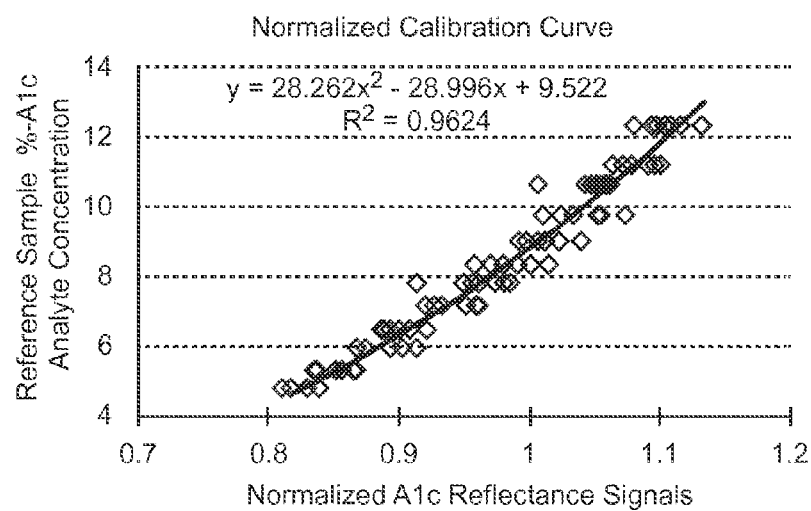
Figure 1E:
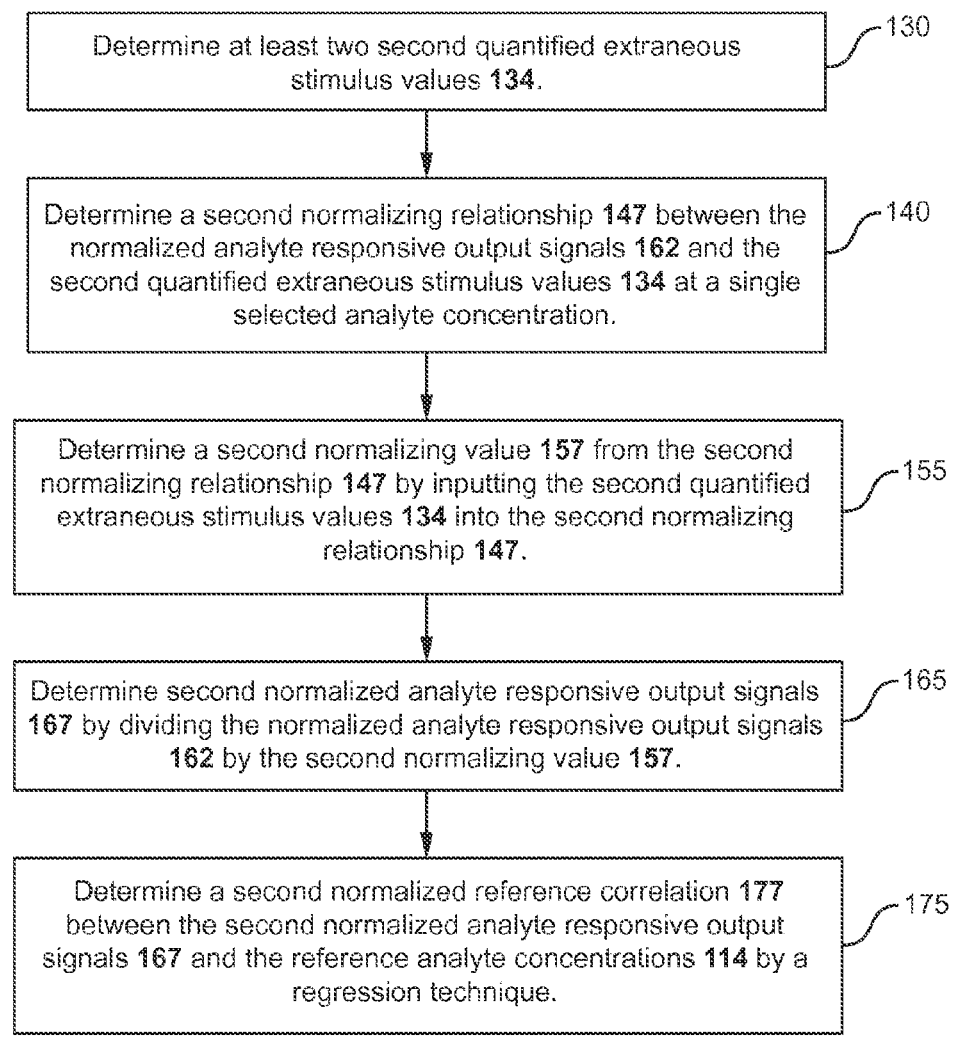
FIG. 1E represents an optional factory calibration method of also considering a second extraneous stimulus with the calibration information.
Figures 1, 1E:
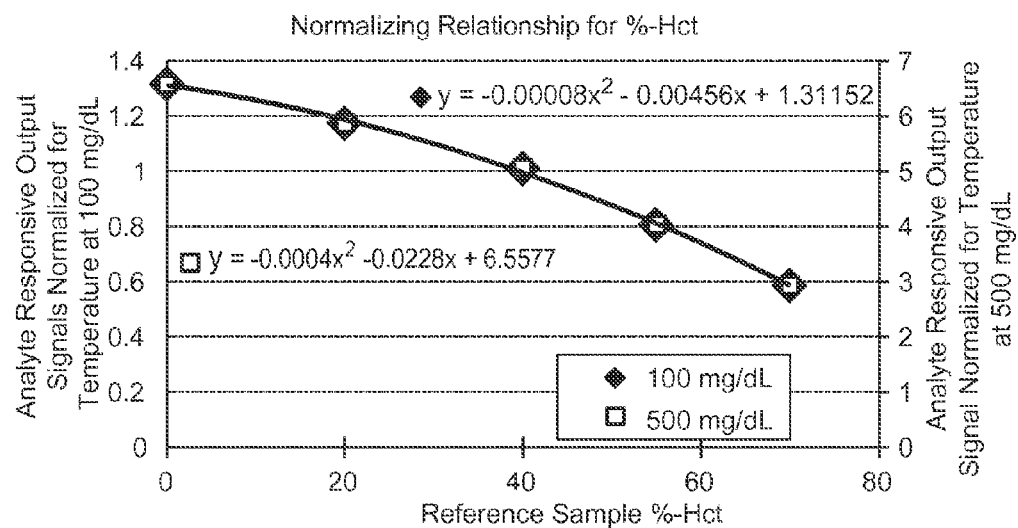
Figures 1, 1E, 2:
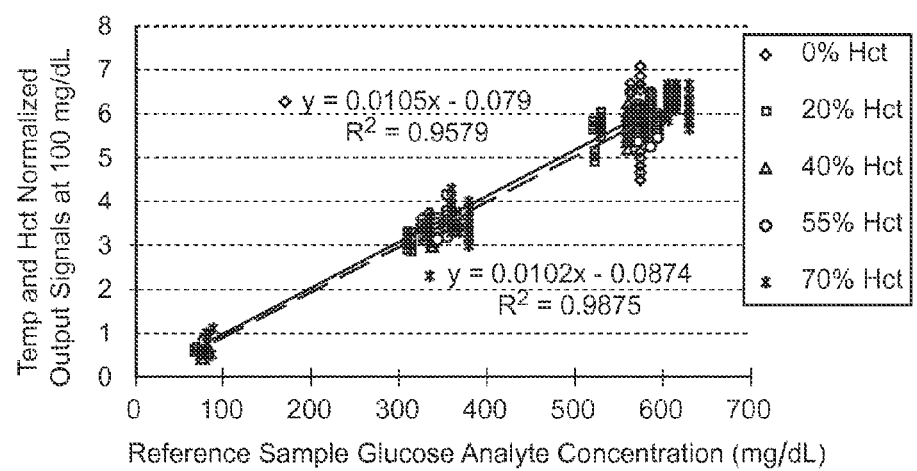

When the at least two analyte responsive output signals 412, 414 are used to determine the first pseudo-reference concentration 435, the measurement device preferably includes calibration information including a normalizing relationship and a normalized reference correlation, as further discussed with regard to FIG. 1D and FIG. 1E. In this case, the general relationship for determining a signal-based anchor parameter 442 for the output signal 412 may be represented as First Channel Signal-Based Anchor Parameter=$(NR_{OSV1}-NR_{Pseudo})/NR_{Pseudo}$ $(dNRCh1/NR_{pseudo})$, where $NR_{OSV1}$ is a first normalized output signal value determined from the first analyte responsive output signal and a normalizing relationship, and $NR_{Pseudo}$ is a pseudo-reference signal determined from the first pseudo-reference concentration 435 with a normalized reference correlation. Similarly, the general relationship for determining a signal-based anchor parameter 444 for the output signal 414 may be represented as Second Channel Signal-Based Anchor Parameter=$(NR_{OSV2}-NR_{Pseudo})/NR_{Pseudo}$ $(dNRCh3/NR_{pseudo})$, where $NR_{OSV2}$ is a second normalized output signal value determined from the second analyte responsive output signal and the normalizing relationship, and $NR_{Pseudo}$ is a pseudo-reference signal determined from the first pseudo-reference concentration 435 with a normalized reference correlation. This signal-based method of determining anchor parameters is further discussed with regard to FIG. 1F.

When initial analyte concentrations determined from the at least two analyte responsive output signals 412, 414 are used to determine the first pseudo-reference concentration 435, the measurement device may include calibration information including a conventional reference correlation or the normalizing relationship and the normalized reference correlation, as further discussed with regard to FIG. 1D and FIG. 1E. In this case, the general relationship for determining a concentration-based anchor parameter 444 for the output signal 412 may be represented as First Channel Concentration-Based Anchor Parameter=(initial analyte concentration determined from the first output signal 412–first pseudo-reference concentration 435)/first pseudo-reference concentration 435. Similarly, the general relationship for determining a concentration-based anchor parameter 446 for the output signal 414 may be represented as Second Channel Concentration-Based Anchor Parameter=(initial analyte concentration determined from the second output signal 414–first pseudo-reference concentration 435)/first pseudo-reference concentration 435. This concentration-based method of determining anchor parameters is further discussed with regard to FIG. 1G. Preferably, the determined first pseudo-reference concentration is closer to the actual analyte concentration of the sample than either initially determined analyte concentrations.

In analysis first compensation determination 450, two or more of the determined anchor parameters (thus, anchor parameter 442 and 444 or anchor parameters 444 and 446) are incorporated into at least two first compensation relationships 452, 453 for the at least two channels to determine independent compensation for the at least two channels. The at least two first compensation relationships 452, 453 determine at least two first anchor compensated analyte concentrations by using the at least two first anchor parameters to provide compensation of the at least two initial analyte concentrations for system error.

System error may be compensated using a residual error compensation technique. Residual error may be expressed generally by Residual Error=total error observed–primary function corrected error. Of the total error in the measured output values, primary compensation removes at least 40% of the error, preferably at least 50%. Thus, in the compensated analyte concentration for each channel, primary compensation removes from 40% to 75% of the total error, and more preferably from 50% to 85%. While error compensation provided by the anchor parameter/s may be used alone, preferably the anchor parameters are used in combination with SSP and other error parameters.

The compensation relationships 452, 453 for the at least two channels may be determined using multi-variant regression or a simpler regression technique using linear or polynomial regression. Preferably, multi-variant regression is used to determine the compensation relationships 452, 453 for the at least two channels in the analysis first compensation determination 450. For either multi-variant or simpler regression techniques, the compensation relationships 452, 453 may be expressed as a relationship of the anchor parameter alone or the anchor parameter and other error parameters. In either case, the at least two first compensation relationships 452, 453 provide compensation of the at least two initial analyte concentrations though the use of at least one first anchor parameter. The compensation relationships 452, 453 may be expressed through the general relationships Ach1_comp=Ach1initial/(1+RECh1) and Ach3_comp=Ach3initial/(1+RECh3), respectively, where Ch1 is channel 1, Ach1_comp is the anchor parameter compensated analyte concentration determined for Ch1, Ach1 initial is the initial analyte concentration determined for Ch1, and RECh1 is the compensation relationship 452 as determined for Ch1, and where Ch3 is channel 3, Ach3_comp is the anchor parameter compensated analyte concentration determined for Ch3, Ach3initial is the initial analyte concentration determined for Ch3, and RECh3 is the compensation relationship 453 as determined for Ch3, as discussed further below.

When the compensation relationships 452, 453 are determined from multi-variant regression or similar mathematical technique, the compensation relationships 452, 453 may compensate for error other than the system error described by the anchor parameters and may incorporate primary compensation with residual compensation. In these techniques, the anchor parameters, which represent system error, may be combined with segmented signal processing (SSP) parameters and other parameters including cross-terms, and ratio parameters, for example, to determine the compensation relationships 452, 453. Thus, the compensation relationship 452 for Ch1 may be represented as RECh1=f(dNRCh1/NR$_{pseudo}$, SSP parameters and other parameters) and the compensation relationship 453 for Ch3 may be represented as RECh3=f(dNRCh3/NR$_{pseudo}$, SSP parameters and other parameters), as previously discussed. The determination of the compensation relationships 452, 453 using multi-variant regression is further discussed with regard to FIG. 1H.

Similarly, a simpler regression technique, such as linear regression may be used to determine the compensation relationships 452, 453. Thus, the compensation relationship 452 for Ch1 may be represented as RECh1=m1*(dNRCh1/NR$_{pseudo}$)+b1. Similarly, the compensation relationship 453 for Ch3 may be represented as RECh3=m3*(dNRCh3/NR$_{pseudo}$)+b3. In these relationships, m1, b1 and m3, b3 are liner regression constants for Ch1 and Ch3, respectively.

In analysis second pseudo-reference concentration determination 454, a second pseudo-reference concentration 455 is determined by averaging an anchor parameter compensated analyte concentration determined from each of the at least two channels of the measurement device. The anchor parameter compensated analyte concentrations determined for the at least two channels are determined using compensation relationships 452, 453 with the initial analyte concentrations of the at least two analyte responsive output signals 412, 414 measured from the test sample, respectively.

A general expression that may be used to determine the individual channel concentrations of the sample may be expressed as Ch1 Concentration=(Ch1A$_{init}$)/(1+RECh1), where Ch1 is channel 1, Ch1A$_{init}$ is the initial analyte concentration of the output signal measured by channel 1 and determined without anchor parameter compensation, and RECh1 is the compensation relationship 452 including the Ch1 anchor parameter. The compensation relationship 453 for Ch3 may be similarly represented as Ch3 Concentration=(Ch3A$_{init}$)/(1+RECh3), where Ch3 is channel 3, Ch3A$_{init}$ is the initial analyte concentration of the output signal measured by channel 3 and determined without anchor parameter compensation, and RECh3 is the compensation relationship 453 including the Ch3 anchor parameter. The analyte concentration determined for the at least two channels of the measurement device is then averaged to provide the second pseudo-reference concentration 455.

In analysis second anchor parameter value determination 460, second anchor parameters are determined for the at least two channels using the second pseudo-reference concentration 455. The determination 460 may be performed similarly as previously described in the first anchor parameter value determination 440, except where the first pseudo-reference concentration 435 is replaced with the second pseudo-reference concentration 455. Preferably, an improved correlation between the true relative error of the analyte concentration (dA/A1c_$_{Ref}$), which is unknown, and the second anchor parameter (dNR/NR$_{pseudo2}$) occurs after each progressive approximation of the pseudo-reference concentration as represented in FIG. 1A.

In analysis second compensation determination 470, the two or more anchor parameters determined in 460 are incorporated into the compensation relationships for the at least two channels 472, 473 to determine the independent compensation for the at least two channels. The analysis second compensation determination 470 is similar to the analysis first compensation determination 450, except that the second pseudo-reference concentration 455 and the second anchor parameters are used to determine the second compensation relationships 472, 473 for the at least two channels. The compensation relationships 472, 473 for the at least two channels may be determined using multi-variant regression or a simpler regression technique using linear or polynomial regression. Preferably, a simpler regression technique is used to determine the compensation relationships 472, 473 for the at least two channels in the analysis second compensation determination 470.

In analysis third pseudo-reference concentration determination 480, a third pseudo-reference concentration 485 is determined by averaging the second anchor parameter compensated analyte concentration determined from the at least two channels of the measurement device. The analyte concentration determined for the at least two channels is determined using the at least two analyte responsive output signals 412, 414 measured from the test sample using the compensation relationships 472, 473, respectively.

A general expression that may be used to determine the individual channel concentrations of the sample may be expressed as Ch1 Concentration=(Ch1A$_{init}$)/(1+RE2Ch1), where Ch1 is channel 1, Ch1A$_{init}$ is the initial analyte concentration of the output signal measured by channel 1 and determined without anchor parameter compensation, and where RE2Ch1 is the compensation relationship 462 including the Ch1 second anchor parameter. The compensation relationship 473 for Ch3 may be similarly represented as Ch3 Concentration=(Ch3$A_{init}$)/(1+RE2Ch3), where Ch3 is channel 3, Ch3$A_{init}$ is the initial analyte concentration of the output signal measured by channel 3 and determined without anchor parameter compensation, and RE2Ch3 is the compensation relationship 473 including the Ch3 second anchor parameter. The analyte concentration determined for the at least two channels of the measurement device is then averaged to provide the third pseudo-reference concentration 485.

If desired, a third anchor parameter may be determined for the at least two channels using the third pseudo-reference concentration 485. Third compensation relationships also may be determined and a fourth pseudo-reference concentration similarly determined, as previously discussed. This process may be repeated until the desired amount of system error has been compensated in the pseudo-reference concentration.

In 490, the second, third, fourth, or additional pseudo-reference concentration may be reported as the compensated final analyte concentration of the sample and may be displayed, stored for future reference, and/or used for additional calculations. Preferably, an improved correlation between the true relative error of the analyte concentration determination, which is unknown, and each progressive anchor parameter occurs after each progressive approximation of the pseudo-reference concentration as represented in FIG. 1A. However, a point of diminishing returns may be reached after two or more pseudo-reference concentrations are determined.

Depending on the improvement in compensation being obtained from each determined anchor parameter, the progressive approximations may be stopped and the selected pseudo-reference concentration at that point in the approximation may be reported as the compensated final analyte concentration of the sample. Each progressively determined anchor parameter preferably has a better correlation with the system error in the pseudo-reference concentration. Thus, when an anchor parameter determined from a pseudo-reference concentration can no longer remove sufficient system error in view of the measurement performance requirements of the biosensor system, the progressive approximation may be stopped and the pseudo-reference concentration at that point in the approximation may be reported as the compensated final analyte concentration of the sample.

FIG. 1D represents a factory calibration method 100 of determining calibration information through a normalization procedure. The factory calibration method 100 is preferably performed during factory calibration of the measurement device of the biosensor system.

In analyte responsive output signal measurement 110, analyte responsive output signals are measured from a reference sample, where the analyte responsive output signals are affected by an extraneous stimulus resulting from a physical characteristic, an environmental aspect, and/or a manufacturing variation error being incorporated into the analyte responsive output signals. At least two analyte responsive output signals are measured. Preferably, at least four, and more preferably at least 6 analyte responsive output signals are measured from the reference sample. Optical and/or electrochemical methods may be used to analyze the reference samples.

In extraneous stimulus quantification 130, one or more extraneous stimulus responsive output signals are measured from the reference samples or the sample environment of the reference samples and the extraneous stimulus quantified to provide at least two quantified extraneous stimulus values 132. The extraneous stimulus responsive output signals may be measured concurrently with the analyte responsive output signals or at different times. Preferably, the stimulus responsive output signals are measured concurrently with the analyte responsive output signals.

The extraneous stimulus may be directly quantified, such as when an optical detector or electrode outputs a specific voltage and/or amperage. The extraneous stimulus may be indirectly quantified, such as when a thermistor provides a specific voltage and/or amperage that is reported as a temperature in degrees Celsius, for example. The extraneous stimulus signals also may be indirectly quantified, such as when the Hct concentration of a sample is determined from a specific voltage and/or amperage measured from an Hct electrode, for example. The extraneous stimulus may be directly or indirectly quantified and then modified to provide the quantified extraneous stimulus values 132, such as when the directly or indirectly quantified extraneous stimulus value is transformed into a concentration. The quantified extraneous stimulus values 132 may be determined by averaging multiple values, such as multiple temperature readings recorded at the same target temperature. The extraneous stimulus may be quantified through other techniques.

In normalizing relationship determination 140, a normalizing relationship 142 is determined using a regression technique from the analyte responsive output signals at a single selected analyte concentration and the quantified extraneous stimulus values 132. FIG. 1D-1 provides an example of how a single analyte concentration was selected in an A1c analysis system and used to determine synthesized extraneous stimulus responsive output signals at the single selected analyte concentration that are responsive to the quantified extraneous stimulus signals for THb.

FIG. 1D-1 shows the individual A1c reflectance signals recorded from the Zone 1 detector/s of the measurement device separated for the four different THb concentrations in blood samples. This allows a single sample analyte concentration to be selected from which synthesized extraneous stimulus responsive output signal values may be determined from the primary output signals. In this example, linear regression lines were determined at each of the 4 THb sample concentrations using the general relationship ($R_{A1c}$=Slope*%-A1c+Int, where $R_{A1c}$ is the output signal from the measurement device, Slope and Int are the slope and intercept, respectively of the linear regression lines at each THb sample concentration, and %-A1c is the sample analyte concentration). Other regression techniques may be used.

The regression equations determined at the 85 THb mg/mL and 230 THb mg/mL are shown on the figure, but regression equations at 127 and 175 mg/mL THb also were determined. In this example, the single selected sample analyte concentration of 9%-A1c was selected to determine the synthesized extraneous stimulus responsive output signal values from the primary output signals. Thus, in this example, the reference sample analyte concentration of 9% provided an ~0.36 A1c synthesized extraneous stimulus responsive output signal value for the 85 mg/mL THb samples from the 85 mg/mL THb regression line and an ~0.44 A1c synthesized extraneous stimulus responsive output signal value for the 230 mg/mL THb samples from the 230 mg/mL THb regression line.

Synthesized extraneous stimulus responsive output signal values can be determined in other ways than determining regression lines and "back determining" a primary output signal value from a selected reference sample analyte concentration. For example, synthesized extraneous stimulus responsive output signal values may be selected from the measured primary output signal values at one reference sample %-A1c concentration for all four THb levels. A single THb reflectance signal measured concurrently was paired with the A1c reflectance signal to form the four pairs of A1c and THb data and to construct the plot of A1c reflectance vs. THb reflectance, which will also lead to the normalizing relationship.

Thus, a synthesized extraneous stimulus responsive output signal was determined at a single selected sample analyte concentration. The synthesized extraneous stimulus responsive output signal may be thought of as the extraneous stimulus responsive output signal extracted from the combined output signal from the measurement device that includes both the primary and the extraneous stimulus. Similarly, the normalizing relationship 142 may be thought of as a reference correlation for the extraneous stimulus.

Linear or non-linear (such as polynomial) regression techniques may be used to determine the normalizing relationship 142. Linear or non-linear regression techniques include those available in the MINITAB® version 14 or version 16 statistical packages (MINTAB, INC., State College, Pa.), Microsoft Excel, or other statistical analysis packages providing regression techniques. Preferably, polynomial regression is used to determine the normalizing relationship 142. For example in MS Excel version 2010, the Linear Trendline Option accessible through the Trendline Layout Chart Tool may be selected to perform linear regression, while the Polynomial Trendline Option may be chosen to perform a non-linear polynomial regression. Other regression techniques may be used to determine the normalizing relationship 142. The normalizing relationship 142 is preferably stored in the measurement device as a portion of the calibration information.

When linear regression is used, the normalizing relationship 142 will be in the form of $Y=mX+b$, where m is the slope and b is the intercept of the regression line. When non-linear regression is used, the normalizing relationship 142 will be in a form of $Y=b_2*X^2+b_1*X+b_0$, and the like, where $b_2$, $b_1$ and $b_0$ are the coefficients of the polynomial. In both the linear or polynomial regression equations, Y is the calculated synthesized extraneous stimulus responsive output signal responsive to the extraneous stimulus at a single selected analyte concentration, and X is the quantified extraneous stimulus signals/values. When a value of X (the quantified extraneous stimulus signal value) is entered into either one of the relationships (linear or polynomial equations), an output value Y, representing the normalizing value (NV) is generated from the normalizing relationship.

If a second extraneous stimulus is adversely affecting the analyte responsive output signals and will be addressed by the calibration information, the normalizing relationship determination 140 is repeated for a second extraneous stimulus.

In normalizing value determination 150, a normalizing value 152 is determined from the normalizing relationship 142 by inputting the quantified extraneous stimulus values 132 into the normalizing relationship 142 and solving for the normalizing value 152.

In normalized output signal determination 160, the analyte responsive output signals are divided by the normalizing value 152 to provide normalized analyte responsive output signals 162. This preferably reduces the effect of the extraneous stimulus on the analyte responsive output signals.

In normalized reference correlation determination 170, a normalized reference correlation 172 is determined between the normalized analyte responsive output signals 162 and reference sample analyte concentrations by a regression technique. Linear or non-linear (such as polynomial) regression techniques may be used, such as those available in the MINITAB® version 14 or version 16 statistical packages (MINTAB, INC., State College, Pa.), Microsoft Excel, or another statistical analysis package providing regression techniques. Preferably, polynomial regression is used to determine the normalized reference correlation 172. For example in MS Excel version 2010, the Linear Trendline Option accessible through the Trendline Layout Chart Tool may be selected to perform linear analysis, while the Polynomial Trendline Option may be chosen to perform a non-linear polynomial analysis. Other regression techniques may be used to determine the normalized reference correlation 172. FIG. 1D-2 represents the determined normalized reference correlation 172 expressed as a normalized calibration curve.

When linear regression is used, the normalized reference correlation 172 will be in the form of $Y=mX+b$, where m is slope and b is an intercept of the regression line. When non-linear regression is used, such as a polynomial, the normalized reference correlation 172 may be in a form of $Y=b_2*X^2+b_1*X+b_0$, and the like, where $b_2$, $b_1$ and $b_0$ are the coefficients of the polynomial. The normalized reference correlation 172 is preferably stored in the measurement device as a portion of the calibration information for later use during the analysis of a sample. In the measurement device, Y is the normalized analyte responsive output signal value determined during the analysis, and X is the analyte concentration of the sample as determined from the normalized reference correlation 172. As discussed further below, for the linear normalized reference correlation, an X value (the sample analyte concentration) may be solved for when inputting a Y value (a value of the normalized output signal) into the equation. For a normalized reference correlation in the form of a $2^{nd}$ order polynomial, the normalized reference correlation 172 may be expressed in the form of a normalized calibration curve as $X=c_2*Y^2+c_1*Y+c_0$ where $c_2$, $c_1$ and $c_0$ are coefficients for the equation. A normalized output signal input to this relationship will generate an analyte concentration.

FIG. 1E represents an optional factory calibration method 102 of also considering a second extraneous stimulus with the calibration information. Thus, FIG. 1D and FIG. 1E may be combined when determining calibration information for the measurement device of the biosensor system. If a second extraneous stimulus adversely affecting the analyte responsive output signals is considered, such as the hematocrit concentration of the sample when the first extraneous stimulus is temperature, at least two second quantified extraneous stimulus values 134 may be determined in accord with the extraneous stimulus quantification 130.

Then a second normalizing relationship 147 may be determined in accord with the normalizing relationship determination 140, but where the second normalizing relationship 147 is determined between the normalized analyte responsive output signals 162 and the second quantified extraneous stimulus at a single selected sample analyte concentration. The second normalizing relationship 147 is preferably stored in the measurement device as a portion of the calibration information. FIG. 1E-1 provides an example of the determination of a second normalizing relationship 147 in a glucose analysis system.

In the case of the second extraneous stimulus, a second normalizing value determination 155 is performed. A second normalizing value 157 is determined from the second normalizing relationship 147 by inputting the second quantified extraneous stimulus values 134 into the second normalizing relationship 147 and solving for the second normalizing value 157.

In the case of the second extraneous stimulus, a second normalized output signal determination 165 is performed. Second normalized analyte responsive output signals 167 are determined by dividing the normalized analyte responsive output signals 162 by the second normalizing value 157. This may be thought of as making the second normalized analyte responsive output signals 167 more responsive to the reference sample analyte concentrations of the sample in relation to the analyte concentrations that would be obtained from the measurement device if the normalized analyte responsive output signals 162 were transformed by the normalized reference correlation 172. FIG. 1E-2 provides an example of determining second normalized analyte responsive output signals 167 in a glucose analysis system.

In the case of the second extraneous stimulus, a second normalized reference correlation determination 175 is performed. A second normalized reference correlation 177 is determined between the second normalized analyte responsive output signals 167 and the reference sample analyte concentrations by a regression technique, as previously described. FIG. 1E-3 provides an example of determining a second normalized reference correlation 177 in a glucose analysis system.

The second normalized reference correlation 177 is preferably stored in the measurement device as a portion of the calibration information. In this case, the normalized reference correlation 172 does not need to be stored in the measurement device and is preferably not used during the analysis. Similarly, three or more extraneous stimuli may be considered by the calibration information, where each extraneous stimulus is represented by an individual normalizing relationship stored in the measurement device in addition to a single normalized reference correlation prepared for the combined extraneous stimuli represented by the individual normalizing relationships.

Figures 1, 1E, 2, 3:
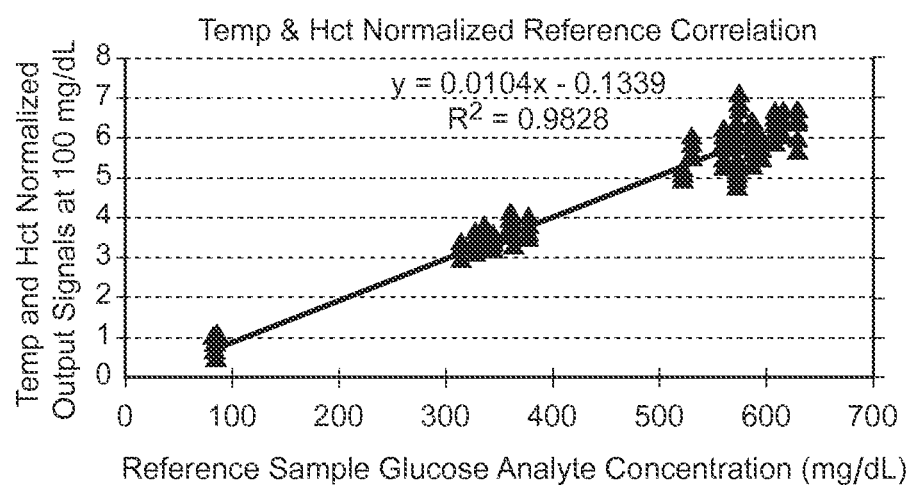
Figure 1F:
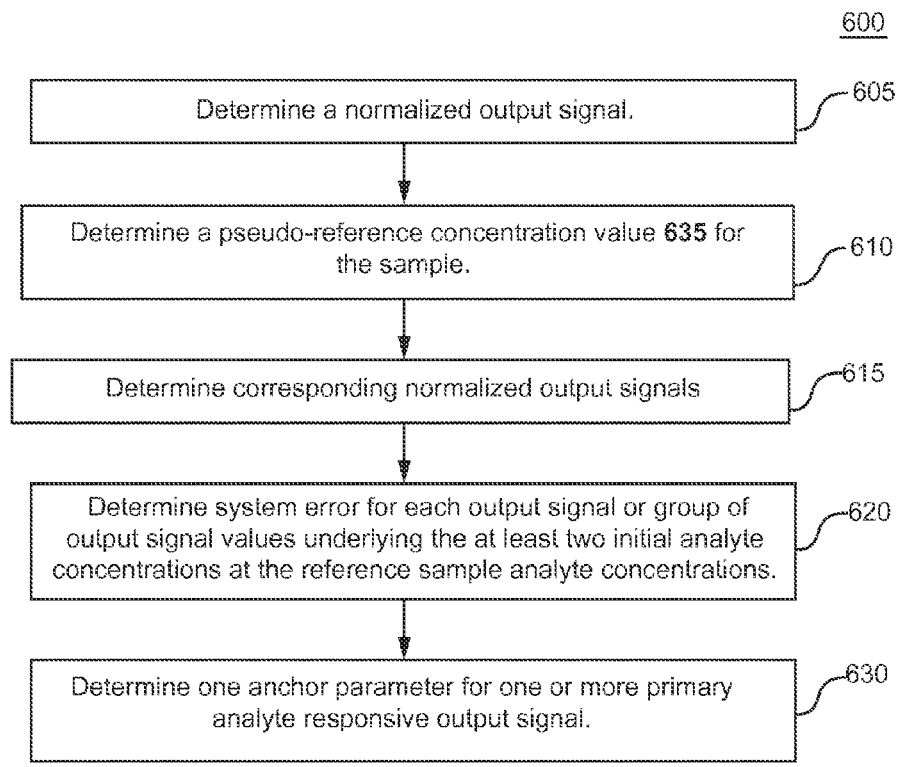
FIG. 1F represents a signal-based method of determining anchor parameters.

FIG. 1F represents a signal-based method 600 of determining anchor parameters. Anchor parameters are determined when the factory calibration information is developed for the desired output signals from the measurement device or the desired normalized output signals. An anchor parameter also is determined during the analysis by the measurement device for compensation. The measurement device includes normalization calibration information as signal-based anchor parameters are determined from the output signals. Preferably, the normalized calibration information includes at least one normalization relationship used to normalize the output signals measured by the measurement device and at least one normalized reference correlation to determine the analyte concentration of the sample from the normalized output signal values.

In 605, at least one normalized output signal ($NR_{act}$) is determined using the normalizing relationship as previously discussed with regard to FIG. B. One or more output signals are generated by the sample using an optical and/or an electrochemical analysis. Each normalized output signal (NRact) is determined by transforming an output signal with the normalizing relationship. Thus, this is performed in the laboratory to determine the compensation relationship 452 as previously described, and during the analysis.

In 610, a pseudo-reference concentration value 635 is determined for the sample by averaging at least two initial analyte concentrations determined from the same sample. The at least two initial analyte concentrations determined from the same sample may be determined from the at least two analyte responsive output signals 412, 414. "Averaging at least two initial analyte concentrations determined from the same sample" also may include initially averaging the at least two analyte responsive output signals 412, 414 and then determining the pseudo-reference from the averaged output signals. Other output signals may be used to determine the at least two initial analyte concentrations. The at least two initial analyte concentrations may be determined in the same way for each of the at least two analyte responsive output signals 412, 414 or the initial analyte concentration determined for each of at least two analyte responsive output signals 412, 414 may be determined in different ways.

Output signals measured by the measurement device and a conventional reference correlation, normalized output signals and a normalized reference correlation, or another method may be used to determine the pseudo-reference concentration. Compensation may or may not be used to determine the initial analyte concentrations that are averaged to provide the pseudo-reference.

In 615, "corresponding normalized output signals" ($NR_{ref}$) are determined by selecting a reference sample analyte concentration from the available reference sample analyte concentrations (horizontal X-Axis) and determining the corresponding normalized output signal value (vertical Y-Axis) through the normalized reference correlation. This is similar to the "process" previously used to determine synthesized output signals with regard to FIG. 1D, however instead of the regression lines being used to convert reference sample analyte concentrations to normalized output signal values, the normalized reference correlation is being used. While this process is described in the context of a graph, in practice only the reference correlation and the selected reference sample analyte concentration may be used. This process is performed in the laboratory for the desired reference sample analyte concentrations.

In 620, system error is determined for each output signal or group of output signal values underlying the at least two initial analyte concentrations at the reference sample analyte concentrations. The system error may be determined for each of the at least two initial analyte concentrations by subtracting the reference sample analyte concentration from an initial analyte concentration determined with the measurement device, and then dividing by the reference sample analyte concentration. As reference sample analyte concentrations are used to determine system error, this is a measure of relative error. This procedure can provide a system error value for each of the reference sample analyte concentrations tested in the laboratory.

The system error values arising from the reference sample analyte concentrations are then preferably used as the target system error values for determining the compensation relationship 452 established from the multi-variant regression. The compensation relationship 452 is preferably stored in the storage medium of the measurement device for use in the analysis of a sample.

In 630, at least one signal-based anchor parameter is determined for one or more primary analyte responsive output signal. Signal-based anchor parameters are determined by subtracting a pseudo-reference signal ($NR_{Pseudo}$) from the normalized output signal ($NR_{measured}$) and dividing by $NR_{Pseudo}$, thus Signal Anchor Parameter=($NR_{measured}$−$NR_{Pseudo}$)/$NR_{Pseudo}$. $NR_{Pseudo}$ is determined similarly to the "corresponding normalized output signals", except in this instance the pseudo-reference concentration is selected from the available reference sample analyte concentrations (horizontal X-Axis) and used to determine the corresponding normalized output signal value (vertical Y-Axis) through the normalized reference correlation. While this process is described in the context of a graph, in practice only the reference correlation and the selected reference sample analyte concentration may be used. This process is performed in the laboratory to determine the compensation relationship 452 as further described. This process also is performed in the measurement device using the pseudo-reference concentration value 635, as at least one anchor parameter is used in the compensation relationship 452.

Figure 1G:
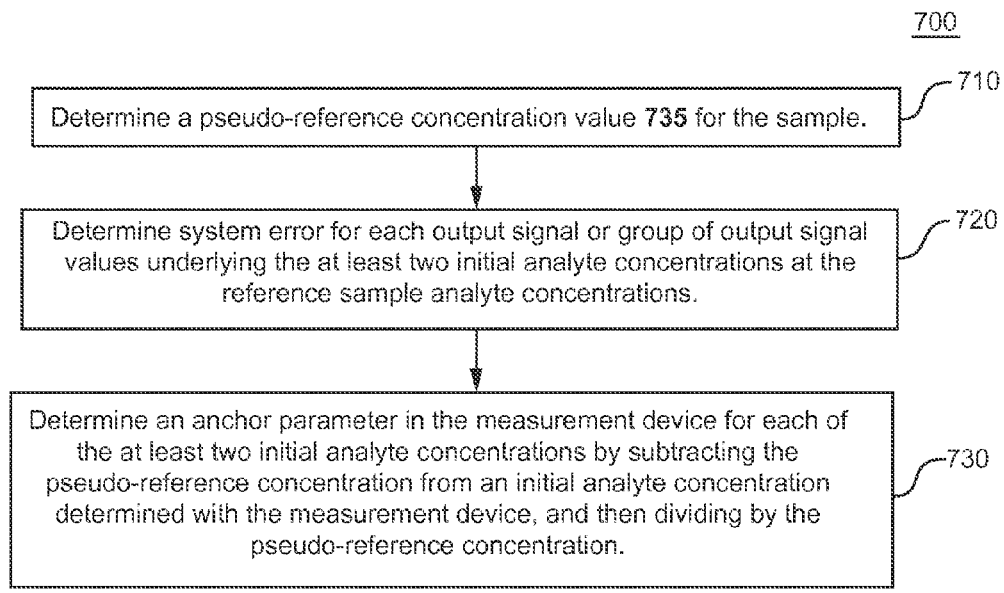
FIG. 1G represents a concentration-based method of determining anchor parameters.

FIG. 1G represents a concentration-based method 700 of determining anchor parameters as previously addressed in 440. The anchor parameters are determined during the analysis by the measurement device. While the measurement device may include normalized calibration information, it is not required as concentration-based anchor parameters are determined from initially determined sample analyte concentrations, not from the output signals.

In 710, a pseudo-reference concentration value 735 may be determined for the sample by averaging at least two initial analyte concentrations determined from the same sample as previously described for method 600. One or more output signals are generated by the sample using an optical and/or an electrochemical analysis. The at least two initial analyte concentrations are determined from the one or more output signals from the sample. Thus, the at least two initial analyte concentrations determined from the same sample may be determined from the at least two analyte responsive output signals 412, 414. "Averaging at least two initial analyte concentrations determined from the same sample" also may include initially averaging the at least two analyte responsive output signals 412, 414 and then determining the pseudo-reference from the averaged output signals. Other output signals may be used to determine the at least two initial analyte concentrations. The at least two initial analyte concentrations may be determined in the same way for each of the at least two analyte responsive output signals 412, 414 or the initial analyte concentration determined for each of the at least two analyte responsive output signals 412, 414 may be determined in different ways.

Output signals measured by the measurement device and a conventional reference correlation, normalized output signals and a normalized reference correlation, or another method may be used to determine the pseudo-reference concentration. Compensation may or may not be used to determine the initial analyte concentrations that are averaged to provide the pseudo-reference.

However, in 710, the pseudo-reference concentration value also may be determined when two initial analyte concentrations are not determined and used to determine a more accurate on average value of sample analyte concentration. In this implementation, normalized calibration information or primary compensation may be used to determine the pseudo-reference concentration value 735.

In 720, system error is determined for each output signal or group of output signal values underlying the at least two initial analyte concentrations at the reference sample analyte concentrations. The system error was determined for each of the at least two initial analyte concentration by subtracting the reference sample analyte concentration from an initial analyte concentration determined with the measurement device, and then dividing by the reference sample analyte concentration. As reference sample analyte concentrations are used to determine system error, this is a measure of relative error. This procedure can provide a system error value for each of the reference sample analyte concentrations tested in the laboratory.

The system error values arising from the reference sample analyte concentrations are then preferably used as the target system error values for determining the compensation relationship 452 established from the multi-variant regression. The compensation relationship 452 is preferably stored in the storage medium of the measurement device for use in the analysis of a sample.

In 730, a concentration-based anchor parameter is determined in the measurement device for each of the at least two initial analyte concentrations by subtracting the pseudo-reference concentration from an initial analyte concentration determined with the measurement device, and then dividing by the pseudo-reference concentration. This provides an anchor parameter for each of the initial analyte concentrations determined by the measurement device during the analysis. One or more of these anchor parameters are then provided to the previously determined compensation relationship 452 as used to provide the final analyte concentration of the sample.

In this case, the general relationship for determining a first anchor parameter 444 may be represented as First Concentration Anchor Parameter=(initial analyte concentration determined from the first output signal 412–pseudo-reference concentration value 435)/pseudo-reference concentration value 435. Similarly, the general relationship for determining a second anchor parameter 446 may be represented as Second Concentration Anchor Parameter=(initial analyte concentration determined from the second output signal 414–pseudo-reference concentration value 435)/pseudo-reference concentration value 435.

Figure 1H:
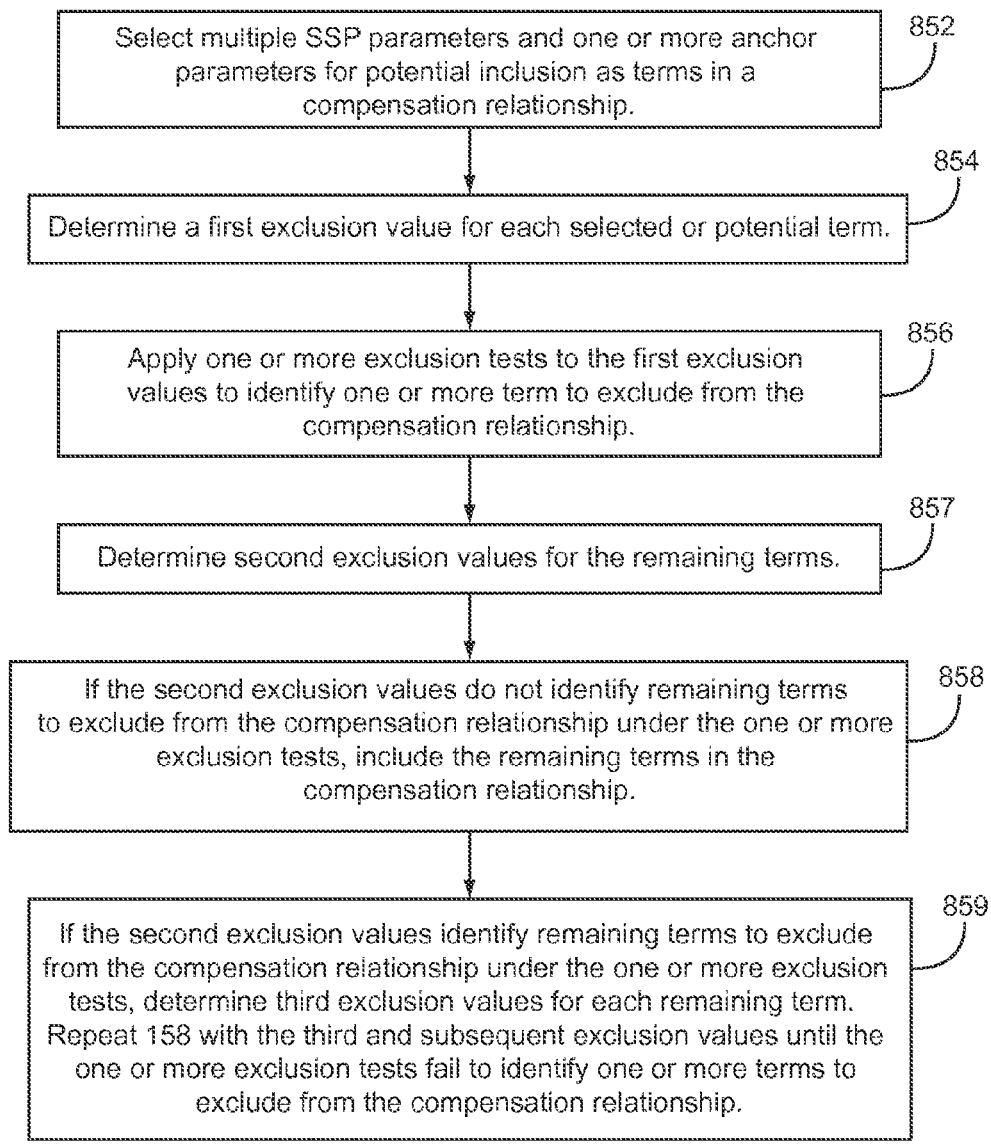
FIG. 1H represents the combination through multi-variant regression of anchor parameters with SSP parameters to determine a compensation relationship.

FIG. 1H represents the combination through multi-variant regression of anchor parameters with segmented signal processing (SSP) parameters to determine a compensation relationship between system error and analyte concentration. The compensation relationship is stored in the storage media of the measurement device of the biosensor system.

In 852, multiple SSP parameters and one or more anchor parameters are selected as terms for potential inclusion in the compensation relationship of the compensation relationship. In addition to the SSP parameters and one or more anchor parameters, other error parameters also may be included in the function, such as cross-terms, measured output signals, and quantified extraneous stimulus. As with the SSP parameters, other error parameters may be obtained from a primary output signal responsive to a light-identifiable species or from the redox reaction of an analyte in a sample of a biological fluid. The error parameters also may be obtained from a secondary output signal independent of the primary output signal, such as from a thermocouple or Hct electrode. The anchor parameters are different from these types of error parameters as the anchor parameters describe system error instead of signal error. The terms of the compensation relationship may include values other than SSP and anchor parameters, including values representing the uncompensated concentration of the analyte in the sample and the like.

Preferably, primary compensation is provided by an index function determined using error parameters from the analysis of the analyte, such as the intermediate signals from the analyte responsive output signal, or from sources independent of the analyte responsive output signal, such as thermocouples, additional electrodes, and the like. Error parameters may be responsive to one or more error contributor affecting the output signal. Thus, the error parameters may be extracted directly or indirectly from the output signal of the analysis and/or obtained independently from the analytic output signal. Other error parameters may be determined from these or other analytic or secondary output signals. Any error parameter may be used to form the term or terms that make up the index function, such as those described in Intl. Pub. No. WO 2009/108239, filed Dec. 6, 2008, entitled "Slope-Based Compensation," and the like.

An index function is responsive to at least one error parameter. An index function may generate a calculated number that correlates total analysis error to an error parameter, such as hematocrit or temperature, and represents the influence of this error parameter on bias. Index functions may be experimentally determined as a regression or other equation relating the deviation of determined analyte concentrations from a reference slope to the error parameter. Thus, the index function represents the influence of the error parameter on the slope deviation, normalized slope deviation, or percent bias arising from the total error in the analysis.

Index functions are complex when they include combinations of terms modified by term weighing coefficients. A complex index function has at least two terms, each modified by a term weighing coefficient. The combination preferably is a linear combination, but other combination methods may be used that provide weighing coefficients for the terms. For example, a complex index function may have a linear combination of terms with weighing coefficients as follows: f(ComplexIndex)=a1+(a2)(R3/2)+(a3)(R4/3)+(a4)(R5/4)+(a5)(R3/2)(G)+(a6)(R4/3)(G)+(a7)(R3/2)(Temp)+(a8)(R4/3)(Temp)+(a9)(Temp)+(a10)(G)+ . . . , where a1 is a constant and not a weighing coefficient, a2-a10 independently are term weighing coefficients, G is the determined analyte concentration of the sample without compensation, and Temp is temperature. Each of the term weighing coefficients (a2-a10) is followed by its associated term—(R3/2), (R4/3), (R5/4), (R3/2)(G), (R4/3)(G), (R3/2)(Temp), (R4/3)(Temp), (Temp), and (G). Other complex index functions may be used including nonlinear and other combinations of terms with weighing coefficients.

Each term in a complex index function may include one or more error parameters. The terms may be selected with one or more exclusion tests. More preferably, primary functions are complex index functions, such as those described in U.S. Pat. Pub. 2011/0297554, entitled "Complex Index Functions", filed Jun. 6, 2011. Other primary compensation techniques may be used.

SSP parameters are calculated from the time-based signal profiles, such as the A1c reflectance profiles or current profiles. Briefly, analysis error and the resultant bias in analyte concentrations determined from the end-point of a previously continuous output signal may be reduced by segmented signal processing (SSP) of the previously continuous output signal. By dividing the continuous output signal into segments, and converting one or more of the segments into an SSP parameter, an SSP function may be determined. Additionally, even in perturbated systems, such as those based on gated amperometry or voltammetry, segmented signal compensation can implement compensation not dependent on the perturbations arising from the gated input signal.

Cross-terms are formed by multiplying individual error parameters. For example, an uncompensated initial sample analyte concentration value and a temperature value. Ratio parameters are formed by dividing individual error parameters. For example, an uncompensated initial sample analyte concentration value and a temperature value. Intermediate currents obtained from the primary output signal at different times during the analysis also may be divided to form ratio parameters. Additional detail regarding cross-terms may be found in U.S. Pat. Pub. 2013/0071869, entitled "Analysis Compensation Including Segmented Signals", filed Sep. 20, 2012. Additional detail regarding ratio parameters may be found in U.S. Pat. Pub. 2011/0231105, entitled "Residual Compensation Including Underfill Error", filed Mar. 22, 2011.

In 854, one or more mathematical techniques are used to determine first exclusion values for each selected or potential term. The mathematical techniques may include regression techniques, preferably multi-variant regression, and the like. The exclusion values may be p-values or the like. The mathematical techniques also may provide weighing coefficients, constants, and other values relating to the selected terms. Multi-variant regression is a type of statistical regression technique that can evaluate the effect of multiple terms on a value and provide information addressing the degree to which each term affects the value. Thus, multi-variant regression can provide both weighing coefficients that address the contribution of each term and p-values addressing the terms that provide the most statistically significant contribution to the value.

MINITAB version 14 or 16 software may be used with the Multi-Variant Regression of Linear Combinations of Multiple Variables option chosen to perform the multi-variant regression. Other statistical analysis or regression options may be used to determine the weighing coefficients for the terms. Additional detail regarding multi-variant regression may be found in U.S. Pat. Pub. 2013/0071869, entitled "Analysis Compensation Including Segmented Signals", filed Sep. 20, 2012 and in U.S. Pat. Pub. 2011/0231105, entitled "Residual Compensation Including Underfill Error", filed Mar. 22, 2011.

In 856, one or more exclusion tests are applied to the exclusion values to identify one or more terms to exclude from the compensation relationship. At least one term is excluded under the test. Preferably, the one or more exclusion tests are used to remove statistically insignificant potential terms from the compensation relationship until the desired terms are obtained for the function. In 857, the one or more mathematical techniques are repeated to identify second exclusion values for the remaining terms. In 858, if the second exclusion values do not identify remaining terms for exclusion from the compensation relationship under the one or more exclusion tests, the remaining terms are included in the compensation relationship. In 859, if the second exclusion values identify remaining terms to exclude from the compensation relationship under the one or more exclusion tests, the one or more mathematical techniques of 857 may be repeated to identify third exclusion values for the remaining terms. These remaining terms may be included in the compensation relationship as in 858 or the process may be iteratively repeated as in 859 until the exclusion test fails to identify one or more terms to exclude. Additional information regarding the use of exclusion tests to determine the terms and weighing coefficients for compensation relationships may be found in U.S. Pat. Pub. 2011/0231105, filed Mar. 22, 2011, entitled "Residual Compensation Including Underfill Error".

Example 1

An example of how channel compensation relationships were determined that included signal-based anchor parameters and other parameters is as follows:

Anchor parameters were used in combination with segmented signal (SSP) and other parameters to provide the compensation relationship for the primary output signal channels Ch1 and Ch3. Multi-variant regression was used to determine a compensation relationship including system error compensation provided by a signal-based anchor parameter (and associated cross-terms) for Ch1 and Ch3 of a %-A1c biosensor system are as follows:

For Ch1 (D-NA1_9)=−0.7729+0.8349*'C2MV'+0.6484*'MR1'−0.005598*'Mt1'+0.7585*'D1-3'+53.16*'D1-5'+16.632*'D2-4'+288.14*'D2-5'+53.16*'D2-20'+0.12334*'D-C2*A1'+4.7018*'DNR1*C2MV'+2.5883*'DNR1*D1-1'−0.019564*'D1-2/1'+0.17053*'D1-2/1a'+3.737'D1-4/1a'+1.6629*'D1-5/3a'+155.92*'DNR1*D1-4/1'+10.458*'DNR1*D1-4/3'.

For Ch3 (D-NA3_9)=−0.7167+0.8591*'C4MV'+0.6088*'MR3'−1.3598*'D3-3'+115.73*'D3-5'+20.958*'D4-4'+204.24*'D4-5'+72.19*'D4-20'+0.27735*'DNR3*A3'−0.3709*'D-C4*A3'−1.453*'DNR3*D3-1'−503.4*'D-C4*D4-4'+4469*'D-C4*D4-20'+0.0916*'D3-2/1a'+1.0911*'D3-4/1'−2.984*'D3-5/3'+1.1017*'D3-5/3a'.

For both compensation relationships, terms such as C4MV are measured reflectance; MR1 is the minimum A1c reflectance measured for an A1c reflectance profile; Mt1 is the analysis time required to reach MR1; terms such as D1-3 are SSP parameters; DNR1 is the anchor parameter for Ch1 and DNR3 is the anchor parameter for Ch3; and terms such as D1-2/1 and D1-2/1a are SSP ratio parameters. The constant is −0.7729 for the Ch1 equation and −0.7167 for the Ch3 equation. The weighing coefficients for each term also are shown. The constant, weighing coefficients, and terms would be different for a different analysis. While one would consider both channels of the measurement device to be "the same", from the terms in the equation as determined through the exclusion process, as previously discussed, the compensation relationship is different for each channel.

The regression output from the multi-variant regression, as performed with MINITAB version 16 software using the Multi-Variant Regression of Linear Combinations of Multiple Variables option is as follows in Table 1. The values on the "Constant" row of the regression output are not weighing coefficients, but a constant for the multi-variant regression equation.

TABLE 1

| Predictor | Coef | SE Coef | T | P |
|---|---|---|---|---|
| A: Ch1 Example of Multi-variant Regression Output with Anchor and Other Parameters. Ch1 - 727 Analyses | | | | |
| Constant | −0.7729 | 0.1194 | −6.47 | 0.000 |
| C2MV | 0.8349 | 0.1434 | 5.82 | 0.000 |
| MR1 | 0.6484 | 0.1978 | 3.28 | 0.001 |
| Mt1 | −0.005598 | 0.001916 | −2.92 | 0.004 |
| D1-3 | 0.7585 | 0.3392 | 2.24 | 0.026 |
| D1-5 | 53.16 | 27.27 | 1.95 | 0.052 |
| D2-4 | 16.632 | 2.484 | 6.70 | 0.000 |
| D2-5 | 288.14 | 43.60 | 6.61 | 0.000 |
| D2-20 | 53.22 | 11.15 | 4.77 | 0.000 |
| D-C2*A1 | 0.12334 | 0.06338 | 1.95 | 0.052 |
| DNR1*C2MV | 4.7018 | 0.5796 | 8.11 | 0.000 |
| DNR1*D1-1 | 2.5883 | 0.8588 | 3.01 | 0.003 |
| D1-2/1 | −0.019564 | 0.005439 | −3.60 | 0.000 |
| D1-2/1a | 0.17053 | 0.02668 | 6.39 | 0.000 |
| D1-4/1a | 3.737 | 1.060 | 3.52 | 0.000 |
| D1-5/3a | 1.6629 | 0.5260 | 3.16 | 0.002 |
| DNR1*D1-4/1 | 155.92 | 36.32 | 4.29 | 0.000 |
| DMR1*D1-4/3 | 10.458 | 5.344 | 1.96 | 0.051 |
| S = 0.0390445; R-Sq = 54.0%; R-Sq(adj) = 52.9% | | | | |
| B: Ch3 Example of Multi-variant Regression Output with Anchor and Other Parameters. Ch3 - 727 Analyses | | | | |
| Constant | −0.7167 | 0.1173 | −6.11 | 0.000 |
| C4MV | 0.8591 | 0.1547 | 5.55 | 0.000 |
| MR3 | 0.6088 | 0.1866 | 3.26 | 0.001 |
| D3-3 | −1.3598 | 0.7734 | −1.76 | 0.079 |
| D3-5 | 115.73 | 45.47 | 2.55 | 0.011 |
| D4-4 | 20.958 | 2.761 | 7.59 | 0.000 |
| D4-5 | 204.24 | 43.78 | 4.66 | 0.000 |
| D4-20 | 72.19 | 12.49 | 5.78 | 0.000 |
| DNR3*A3 | 0.27735 | 0.03963 | 7.00 | 0.000 |
| D-C4*A3 | −0.3709 | 0.1163 | −3.19 | 0.001 |
| DNR3*D3-1 | −1.4530 | 0.5336 | −2.72 | 0.007 |
| D-C4*D4-4 | −503.4 | 221.3 | −2.28 | 0.023 |
| D-C4*D4-20 | 4469 | 2452 | 1.82 | 0.069 |
| D3-2/1a | 0.09160 | 0.01080 | 8.48 | 0.000 |
| D3-4/1 | 1.0911 | 0.2548 | 4.28 | 0.000 |
| D3-5/3 | −2.984 | 1.310 | −2.28 | 0.023 |
| D3-5/3a | 1.1017 | 0.3882 | 2.84 | 0.005 |
| S = 0.0395936; R-Sq = 55.7%; R-Sq(adj) = 54.8% | | | | |

Example 2

An example of how channel compensation relationships were determined that included concentration-based anchor parameters and other parameters is as follows:

In this example, system error was generally expressed for each channel by writing relative error (dA/A1cRef or dA3/A1cRef) as a function of a concentration anchor parameter combined with SSP and other parameters as follows: DAr1=dA1/A1cRef=f(DA1=anchor parameter (dA1/A1cAvg), SSP parameters, and other error parameters for Ch1); DAr3=dA3/A1cRef=f(DA3=anchor parameter (dA3/A1cAvg), SSP parameters, and other error parameters for Ch3). These expressions were determined in the laboratory for multiple samples having known reference sample analyte concentrations as determined with a Tosoh G7 reference instrument.

An example of this method to provide a compensation relationship based on anchor parameters in combination with SSP and other parameters is as follows. Table 2A and Table 2B show the multi-variable regression results obtained by including the concentration-based anchor parameter and its cross-terms with the SSP and other parameters for Ch1 and Ch3. The values on the "Constant" row of the regression output are not weighing coefficients, but a constant for the multi-variant regression equation.

TABLE 2A

| Ch1 Multi-variant Regression Results from Anchor, SSP, and Other Parameters. Ch1 Regression Analysis: DAr1 versus C2MV, D1-5, . . . Anchor parameter DA1 and associate cross terms with SSP and other parameters | | | | |
|---|---|---|---|---|
| Predictor | Coef | SE Coef | T | P |
| Constant | −0.3422 | 0.1034 | −3.31 | 0.001 |
| C2MV | 0.3060 | 0.1398 | 2.19 | 0.029 |

TABLE 2A-continued

Ch1 Multi-variant Regression Results from Anchor, SSP, and Other Parameters.
Ch1 Regression Analysis: DAr1 versus C2MV, D1-5, . . .
Anchor parameter DA1 and associate cross terms with SSP and other parameters

| Predictor | Coef | SE Coef | T | P |
|---|---|---|---|---|
| D1-5 | 159.82 | 21.50 | 7.43 | 0.000 |
| DA1*C2MV | 1.7524 | 0.8266 | 2.12 | 0.034 |
| DA1*D1-3a | 70.04 | 18.04 | 3.88 | 0.000 |
| DA1*D1-3 | −53.73 | 14.30 | −3.76 | 0.000 |
| D1-2/1 | −0.020109 | 0.004088 | −4.92 | 0.000 |
| DA1*D1-4/1a | 255.82 | 46.75 | 5.47 | 0.000 |
| DA1*D1-4/3 | 15.856 | 3.538 | 4.48 | 0.000 |
| DA1*D1-5/3 | −156.14 | 31.87 | −4.90 | 0.000 |
| DA1*D1-5/3a | 98.25 | 25.06 | 3.92 | 0.000 |
| MR1*D1-2/1a | 0.54276 | 0.07503 | 7.23 | 0.000 |
| Mt1*D1-4/3a | −0.017550 | 0.006175 | −2.84 | 0.005 |

S = 0.0438916
R-Sq = 42.8%
R-Sq(adj) = 41.8%

TABLE 2B

Ch3 Multi-variant Regression Results from Anchor, SSP, and Other Parameters.
Ch3 Regression Analysis: DAr3 versus DA3, MR3, . . .
Anchor parameter DA3 and associate cross terms with SSP and other parameters

| Predictor | Coef | SE Coef | T | P |
|---|---|---|---|---|
| Constant | −0.28165 | 0.04108 | −6.86 | 0.000 |
| DA3 | 5.151 | 2.469 | 2.09 | 0.037 |
| MR3 | 0.9509 | 0.1917 | 4.96 | 0.000 |
| D3-2 | −0.08559 | 0.01792 | −4.78 | 0.000 |
| D3-5 | 135.87 | 21.10 | 6.44 | 0.000 |
| DA3*C4MV | −5.699 | 3.401 | −1.68 | 0.094 |
| D3-4/1a | 4.513 | 1.453 | 3.11 | 0.002 |
| D3-4/2a | 0.11812 | 0.05092 | 2.32 | 0.021 |
| D3-4/2 | −1.4066 | 0.6425 | −2.19 | 0.029 |
| DA3*D3-4/1 | −9.629 | 5.368 | −1.79 | 0.073 |
| MR3*D3-4/2a | −0.5884 | 0.2514 | −2.34 | 0.020 |
| Mt3*D3-3/1a | −0.0020053 | 0.0009756 | −2.06 | 0.040 |
| Mt3*D3-3/2 | 0.009898 | 0.004138 | 2.39 | 0.017 |

S = 0.0436156
R-Sq = 46.6%
R-Sq(adj) = 45.7%

%-A1c Analyses of Blood

Analyte concentrations were determined for multiple reference samples for Channel 1 (Ch1) and for Channel 3 (Ch3) with the measurement device to provide two initial %-A1c analyte concentrations. Thus, for each sample, a Ch1 initial analyte concentration (Ch1A1c_$Init$) and a Ch3 initial analyte concentration (Ch3A1c_$Init$) was determined. A first pseudo-reference (Pseudo1) was then determined by averaging the Ch1 and Ch3 initial %-A1c analyte concentrations. Anchor parameters were determined using multi-variant regression using SSP and other parameters to determine anchor parameter compensated analyte concentrations for Ch1 and Ch3, as previously discussed. As previously described, progressive approximations of the pseudo-reference concentration were then performed to further reduce the error in the pseudo-reference concentration selected as the compensated final analyte concentration of the sample.

Figure 2A:
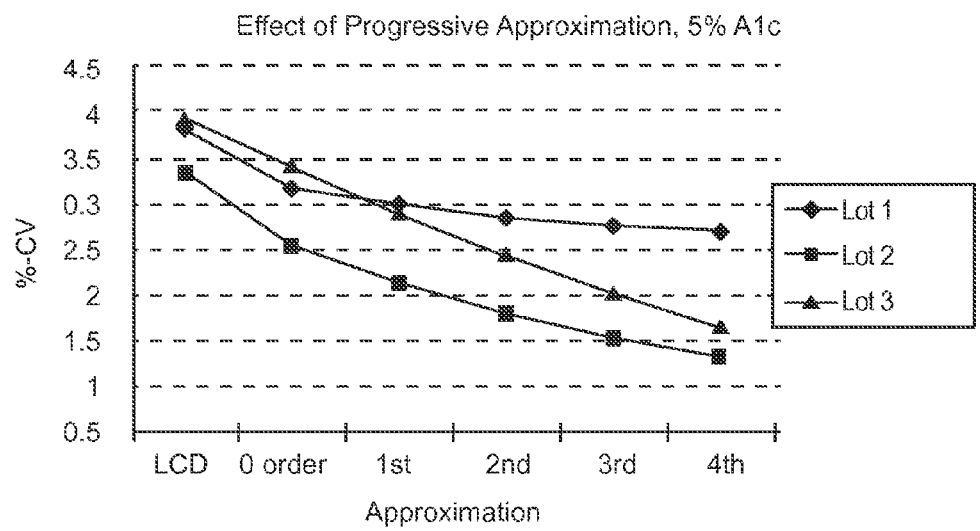
FIG. 2A and FIG. 2B represent two examples of progressive approximation of pseudo-reference concentrations for a set of reference samples of blood including 5% or 9% of the A1c analyte.
Figure 2B:
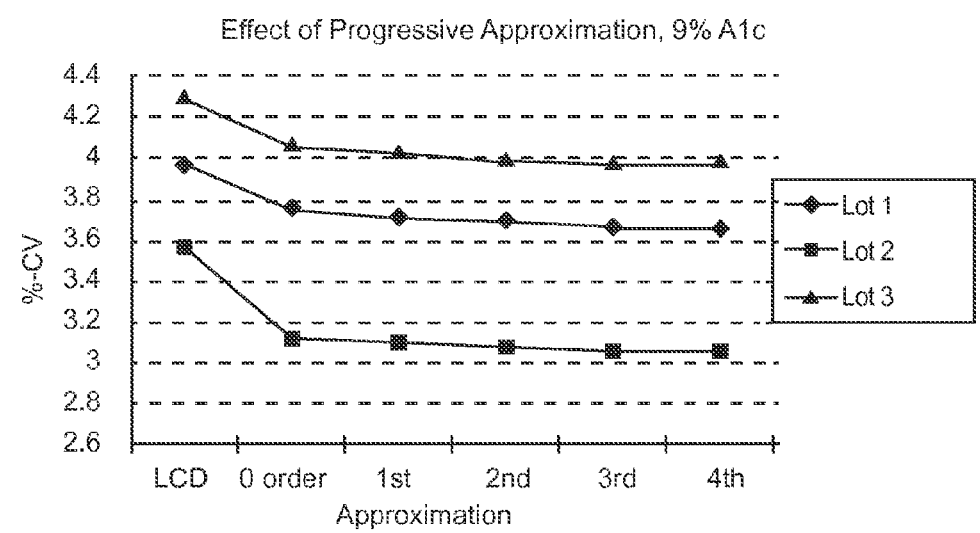

FIG. 2A and FIG. 2B represent two examples of progressive approximation of pseudo-reference concentrations for a set of reference samples of blood including 5% or 9% of the A1c analyte. At each %-A1c level, the analysis was repeated about 50 times for three lots of test sensors. These two sets of plots establish that after the initial anchor parameter compensation (compensation relationships for Ch1 and Ch3 including anchor parameter, SSP, and other parameters in the multi-variable regression), the %-CV values continued to improve in the later progressive approximations of the pseudo-reference concentration. The horizontal X-Axis of the plots show the %-CV in sample analyte concentrations determined without anchor-parameter (system error) compensation (LCD), a first pseudo-reference concentration (0 order), a second pseudo-reference concentration ($1^{st}$ progressive approximation), a third pseudo-reference concentration ($2^{nd}$ progressive approximation), a fourth pseudo-reference concentration ($3^{rd}$ progressive approximation), and a fifth pseudo-reference concentration ($4^{th}$ progressive approximation).

In FIG. 2A, at the 5%-A1c sample concentration %-CV dropped from about 3.7 for the non-anchor parameter compensated concentrations to about 2 for the $4^{th}$ approximation using progressive approximation of the pseudo-reference concentration. Thus, an improvement approaching 50% was observed for %-CV which would translate into significantly improved measurement performance for the biosensor system. In FIG. 2B, at the 9%-A1c sample concentration %-CV dropped from about 3.7 for the non-anchor parameter compensated concentrations to about 3.5 for the $4^{th}$ approximation using progressive approximation of the pseudo-reference concentration. Stepwise %-CV improvement continued after the 0 order approximation.

Figure 2C:
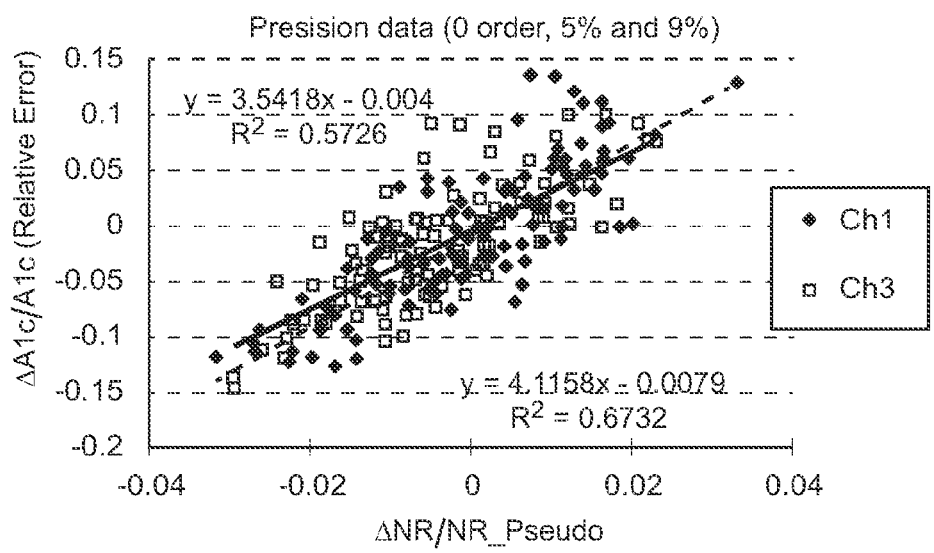
FIG. 2C and FIG. 2D show the regressions for the 0 order and $4^{th}$ progressive approximations for the Ch1 and Ch3 detectors of Zone 1 (the primary output signals) for the analysis data obtained with the Lot 2 test sensors and the measurement device of the biosensor system.
Figure 2D:
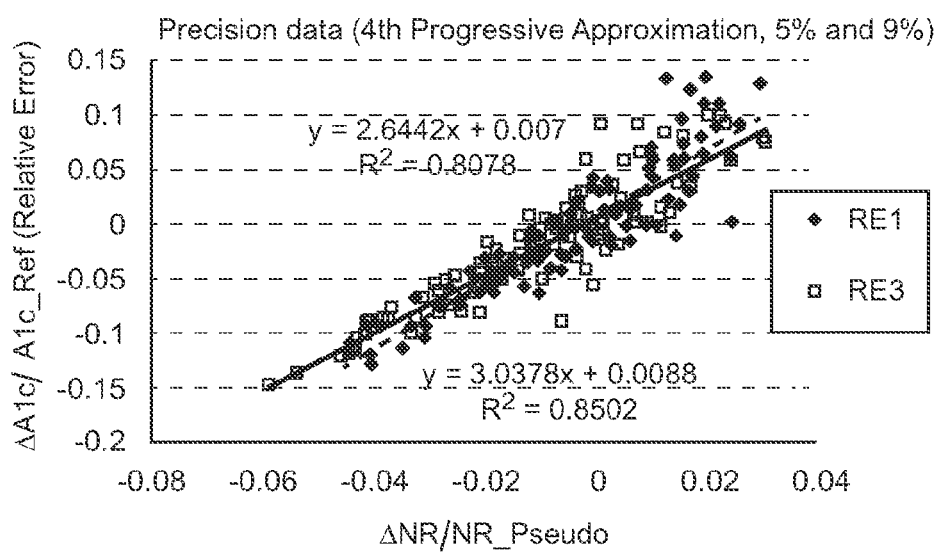

FIG. 2C and FIG. 2D show the regressions for the 0 order and $4^{th}$ progressive approximations for the Ch1 and Ch3 detectors of Zone 1 (the primary output signals) for the analysis data obtained with the Lot 2 test sensors and the measurement device of the biosensor system. A significant improvement of approximately 27% (0.85−0.67/0.67*100) was noted for the $R^2$ correlation values after the $4^{th}$ progressive approximation, thus, showing the increased ability of the progressive approximation compensation to describe the error in the determined analyte concentrations.

Figure 2E:
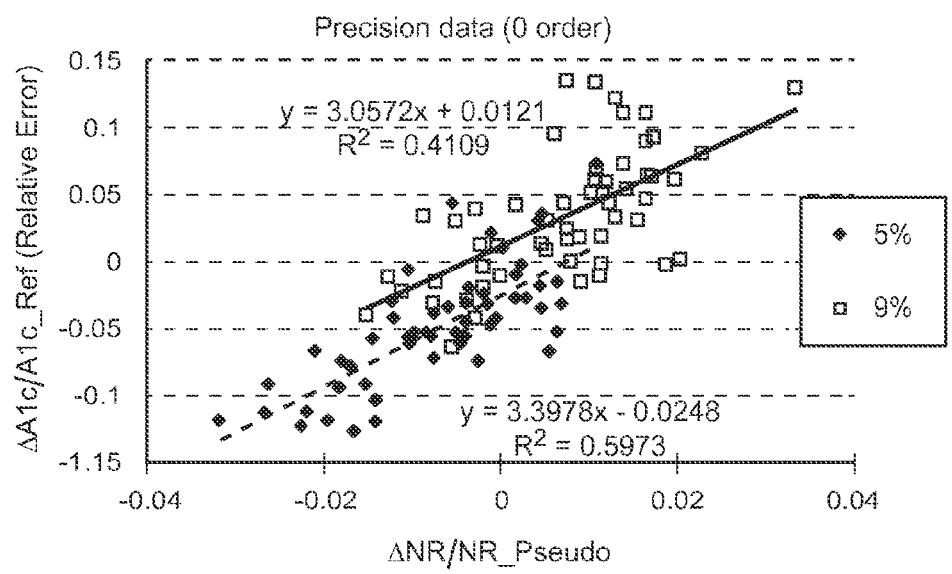
FIG. 2E and FIG. 2F show the regressions separately for the 5% and 9% A1c concentrations for the Ch1 data for the 0 order and $4^{th}$ progressive approximations.
Figure 2F:
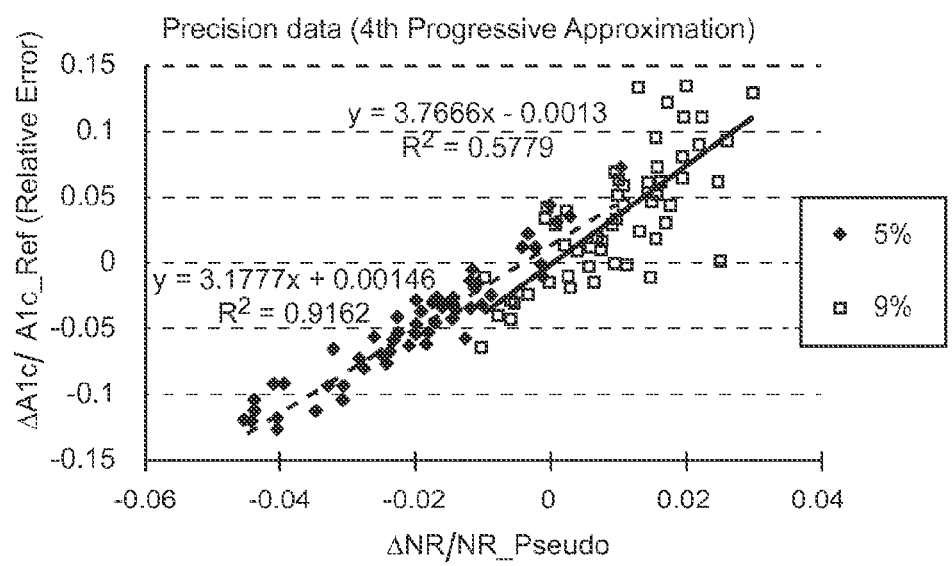

FIG. 2E and FIG. 2F show the regressions separately for the 5% and 9% A1c concentrations for the Ch1 data for the 0 order and $4^{th}$ progressive approximations. Here, the ability of the progressive approximation compensation allowed for a near twofold increase in the ability of the biosensor system to describe the error in the analyses at the lower 5% sample analyte concentration.

Figure 2G:
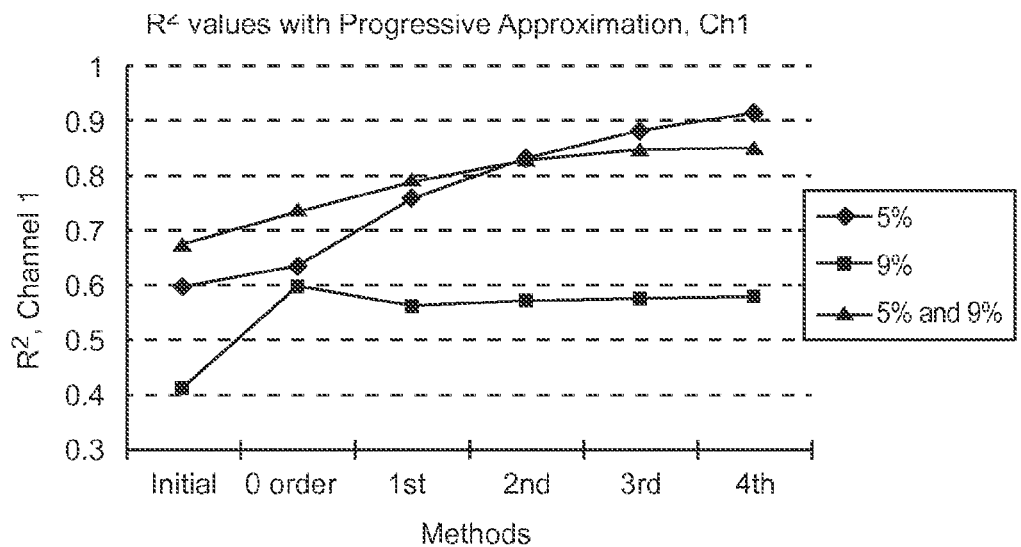
FIG. 2G and FIG. 2H show the $R^2$ correlation values for the progressive approximation of pseudo-reference concentrations for the multiple analyses for the two separate channels.
Figure 2H:
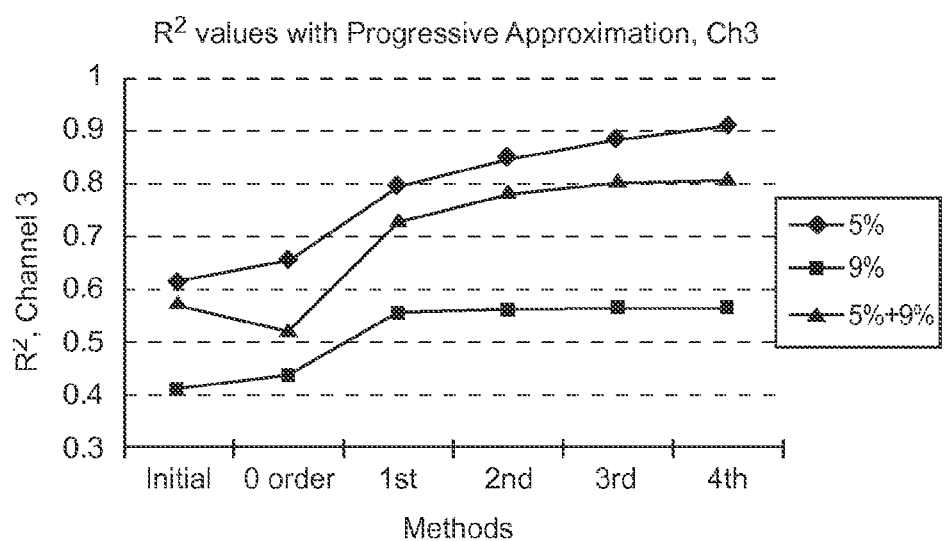
Figure 3:
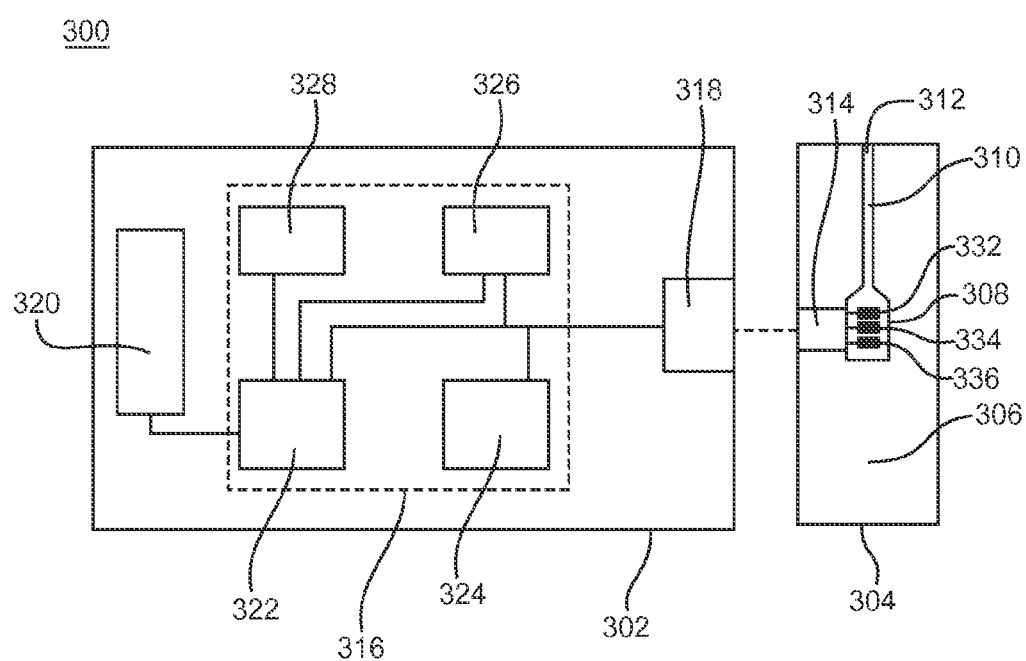

FIG. 2G and FIG. 2H show the $R^2$ correlation values for the progressive approximation of pseudo-reference concentrations for the multiple analyses for the two separate channels. As the $R^2$ values increased, the %-CV values (representing precision) also improved, especially at the 5% A1c sample concentration. Thus, an improvement in measurement performance was observed for the biosensor system.

FIG. 3 depicts a schematic representation of a biosensor system 300 that determines an analyte concentration in a sample of a biological fluid. Biosensor system 300 includes a measurement device 302 and a test sensor 304. The measurement device 302 may be implemented in an analytical instrument, including a bench-top device, a portable or hand-held device, or the like. Preferably the measurement device 302 is implemented in a hand-held device.

The measurement device 302 and the test sensor 304 may be adapted to implement an electrochemical sensor system, an optical sensor system, a combination thereof, or the like.

The biosensor system 300 determines the analyte concentration of the sample using conventional calibration information or the calibration information developed in accord with the previously described normalization techniques and anchor parameter compensation information stored in the measurement device 302. The calibration information from one or both of the calibration methods 100 and 102 may be stored in the measurement device 302. The analysis method 400 may be stored in the measurement device for implementation by the biosensor system 300.

When compensation is implemented by the biosensor system 300, the anchor parameter compensation information determined from the progressive approximation of pseudo-reference concentrations may improve the measurement performance of the biosensor system 300 in determining the analyte concentration of the sample. The biosensor system 300 may be utilized to determine analyte concentrations, including those of glucose, A1c, uric acid, lactate, cholesterol, bilirubin, and the like. While a particular configuration is shown, the biosensor system 300 may have other configurations, including those with additional components.

The test sensor 304 has a base 306 that forms a reservoir 308 and a channel 310 with an opening 312. The reservoir 308 and the channel 310 may be covered by a lid with a vent. The reservoir 308 defines a partially-enclosed volume. The reservoir 308 may contain a composition that assists in retaining a liquid sample such as water-swellable polymers or porous polymer matrices. Reagents may be deposited in the reservoir 308 and/or the channel 310. The reagents may include one or more enzymes, binders, mediators, and like species. The reagents may include a chemical indicator for an optical system. The test sensor 304 has a sample interface 314 adjacent to the reservoir 308. The test sensor 304 may have other configurations.

In an optical sensor system, the sample interface 314 has an optical portal or aperture for viewing the sample. The optical portal may be covered by an essentially transparent material. The sample interface 314 may have optical portals on opposite sides of the reservoir 308.

In an electrochemical system, the sample interface 314 has conductors connected to a working electrode 332 and a counter electrode 334 from which the analytic output signal may be measured. The sample interface 314 also may include conductors connected to one or more additional electrodes 336 from which secondary output signals may be measured. The electrodes may be substantially in the same plane or in more than one plane. The electrodes may be disposed on a surface of the base 306 that forms the reservoir 308. The electrodes may extend or project into the reservoir 308. A dielectric layer may partially cover the conductors and/or the electrodes. The sample interface 314 may have other electrodes and conductors.

The measurement device 302 includes electrical circuitry 316 connected to a sensor interface 318 and an optional display 320. The electrical circuitry 316 includes a processor 322 connected to a signal generator 324, an optional temperature sensor 326, and a storage medium 328.

The signal generator 324 is capable of providing an electrical input signal to the sensor interface 318 in response to the processor 322. In optical systems, the electrical input signal may be used to operate or control the detector and light source in the sensor interface 318. In electrochemical systems, the electrical input signal may be transmitted by the sensor interface 318 to the sample interface 314 to apply the electrical input signal to the sample of the biological fluid. The electrical input signal may be a potential or current and may be constant, variable, or a combination thereof, such as when an AC signal is applied with a DC signal offset. The electrical input signal may be applied continuously or as multiple excitations, sequences, or cycles. The signal generator 324 also may be capable of recording an output signal from the sensor interface as a generator-recorder.

The optional temperature sensor 326 is capable of determining the ambient temperature of the measurement device 302. The temperature of the sample may be estimated from the ambient temperature of the measurement device 302, calculated from the output signal, or presumed to be the same or similar to the ambient temperature of the measurement device 302. The temperature may be measured using a thermister, thermometer, or other temperature sensing device. Other techniques may be used to determine the sample temperature.

The storage medium 328 may be a magnetic, optical, or semiconductor memory, another storage device, or the like. The storage medium 328 may be a fixed memory device, a removable memory device, such as a memory card, remotely accessed, or the like.

The processor 322 is capable of implementing the analyte analysis method using computer readable software code and the calibration information and anchor parameter compensation information determined from the progressive approximation of pseudo-reference concentrations stored in the storage medium 328. The processor 322 may start the analyte analysis in response to the presence of the test sensor 304 at the sensor interface 318, the application of a sample to the test sensor 304, in response to user input, or the like. The processor 322 is capable of directing the signal generator 324 to provide the electrical input signal to the sensor interface 318. The processor 322 is capable of receiving the sample temperature from the temperature sensor 326. The processor 322 is capable of receiving the output signals from the sensor interface 318.

In electrochemical systems, the analyte responsive primary output signal is generated from the working and counter electrodes 332, 334 in response to the reaction of the analyte in the sample. Secondary output signals also may be generated from additional electrodes 336. In optical systems, the detector or detectors of the sensor interface 318 receive the primary and any secondary output signals. The output signals may be generated using an optical system, an electrochemical system, or the like. The processor 322 is capable of determining analyte concentrations from output signals using the calibration information and the anchor parameter compensation information determined from the progressive approximation of pseudo-reference concentrations stored in the storage medium 328. The results of the analyte analysis may be output to the display 320, a remote receiver (not shown), and/or may be stored in the storage medium 328.

The calibration information relating reference sample analyte concentrations and output signals from the measurement device 302 and the anchor parameter compensation information determined from the progressive approximation of pseudo-reference concentrations may be represented graphically, mathematically, a combination thereof, or the like. The calibration information and anchor parameter compensation information determined from the progressive approximation of pseudo-reference concentrations are preferably represented as correlation equations, which may be represented by a program number (PNA) table, another look-up table, or the like that is stored in the storage medium 328.

Instructions regarding implementation of the analyte analysis including calibration and anchor parameter compensation information determined from the progressive approximation of pseudo-reference concentrations also may be provided by the computer readable software code stored in the storage medium 328. The code may be object code or any other code describing or controlling the described functionality. The data from the analyte analysis may be subjected to one or more data treatments, including the determination of decay rates, K constants, ratios, functions, and the like in the processor 322.

In electrochemical systems, the sensor interface 318 has contacts that connect or electrically communicate with the conductors in the sample interface 314 of the test sensor 304. The sensor interface 318 is capable of transmitting the electrical input signal from the signal generator 324 through the contacts to the connectors in the sample interface 314. The sensor interface 318 also is capable of transmitting the output signal from the sample through the contacts to the processor 322 and/or signal generator 324.

In light-absorption and light-generated optical systems, the sensor interface 318 includes a detector that collects and measures light. The detector receives light from the test sensor 304 through the optical portal in the sample interface 314. In a light-absorption optical system, the sensor interface 318 also includes a light source such as a laser, a light emitting diode, or the like. The incident beam may have a wavelength selected for absorption by the reaction product. The sensor interface 318 directs an incident beam from the light source through the optical portal in the sample interface 314. The detector may be positioned at an angle such as 45° to the optical portal to receive the light reflected back from the sample. The detector may be positioned adjacent to an optical portal on the other side of the sample from the light source to receive light transmitted through the sample. The detector may be positioned in another location to receive reflected and/or transmitted light.

The optional display 320 may be analog or digital. The display 320 may include a LCD, a LED, an OLED, a vacuum fluorescent display (VFD), or other display adapted to show a numerical reading. Other display technologies may be used. The display 320 electrically communicates with the processor 322. The display 320 may be separate from the measurement device 302, such as when in wireless communication with the processor 322. Alternatively, the display 320 may be removed from the measurement device 302, such as when the measurement device 302 electrically communicates with a remote computing device, medication dosing pump, and the like.

In use, a liquid sample for analysis is transferred into the reservoir 308 by introducing the liquid to the opening 312. The liquid sample flows through the channel 310, filling the reservoir 308 while expelling the previously contained air. The liquid sample chemically reacts with the reagents deposited in the channel 310 and/or reservoir 308.

The test sensor 302 is disposed in relation to the measurement device 302, such that the sample interface 314 is in electrical and/or optical communication with the sensor interface 318. Electrical communication includes the transfer of input and/or output signals between contacts in the sensor interface 318 and conductors in the sample interface 314. Optical communication includes the transfer of light between an optical portal in the sample interface 314 and a detector in the sensor interface 318. Optical communication also includes the transfer of light between an optical portal in the sample interface 314 and a light source in the sensor interface 318.

The processor 322 is capable of directing the signal generator 324 to provide an input signal to the sensor interface 318 of the test sensor 304. In an optical system, the sensor interface 318 is capable of operating the detector and light source in response to the input signal. In an electrochemical system, the sensor interface 318 is capable of providing the input signal to the sample through the sample interface 314. The test sensor 304 is capable of generating one or more output signals in response to the input signal. The processor 322 is capable of receiving the output signals generated in response to the redox reaction of the analyte in the sample as previously discussed.

The processor 322 is capable of transforming the output signal using the analysis method and the calibration information stored in the storage medium 328 to determine an initial analyte concentration of the sample. The processor 322 may then report this initial analyte concentration. The processor 322 is capable of implementing anchor parameter compensation including the progressive approximation of pseudo-reference concentrations to determine the final analyte concentration of the sample. More than one compensation and/or other function also may be implemented by the processor 322.

To provide a clear and more consistent understanding of the specification and claims of this application, the following definitions are provided.

"Average" or "Averaged" or "Averaging" includes the combination of two or more variables to form an average variable. A variable may be a numerical value, an algebraic or scientific expression, or the like. For example, averaging may be performed by adding the variables and dividing the sum by the number of variables; such as in the equation $AVG=(a+b+c)/3$, where AVG is the average variable and a, b, and c are the variables. In another example, averaging includes modifying each variable by an averaging coefficient and then adding the modified variables to form a weighted average; such as in the equation $W_{AVG}=0.2*a+0.4*b+0.4*c$, where $W_{AVG}$, is the weighted average, 0.2, 0.4 and 0.4 are the averaging coefficients, and a, b, and c are the variables. The averaging coefficients are numbers between 0 and 1; and if added, will provide a sum of 1 or substantially 1. Other averaging methods may be used.

"Weighing Coefficients" apportion the contribution of each term to the relationship. Weighing coefficients are numbers between 0 and 1, but excluding 0 and 1, and if added, will provide a sum of 1 or substantially 1. A weighing coefficient cannot be 1 as it does not apportion the contribution of the term to the relationship, and a weighing coefficient cannot be 0, as it results in the exclusion of the term from the relationship. Thus, weighing coefficients allow for each term to have a different apportionment to the relationship. Two or more of the term weighing coefficients may be the same or similarly apportion the contribution of their respective terms to the function. However, at least two weighing coefficients are different or differently apportion the contribution of their respective terms to the relationship. In this way, the term weighing coefficients may be selected to allow for the effect of one term on another term in relation to the overall function, thus reducing or eliminating error from the interactions of the terms when a complex index function is used. The term weighing coefficients are not a single value or constant that may be applied by algebraic disposition to all the terms. The weighing coefficients for terms may be determined through a mathematical technique, such as the statistical processing of the data collected from a combination of multiple analyte concentrations, different hematocrit levels, different total hemoglobin levels, different temperatures, and the like. Weighing coefficients for the terms may be determined through other mathematical techniques including different statistical processing methods.

Preferably, multi-variant regression techniques including one or more exclusion tests are used to determine weighing coefficients for the terms.

A "complex index function" is an index function having terms modified by weighing coefficients. A complex index function preferably is not "complex" in a mathematical sense, thus does not require or imply the use of an imaginary number (a number with the square root of negative one). However, a complex index function may include one or more imaginary numbers, but is not limited or restricted to having any imaginary numbers.

"Measurable species" addresses a species the biosensor system is designed to determine the presence and/or concentration of in the sample and may be the analyte of interest or a mediator whose concentration in the sample is responsive to that of the analyte of interest.

While various embodiments of the invention have been described, it will be apparent to those of ordinary skill in the art that other embodiments and implementations are possible within the scope of the invention.

What is claimed is:

1. A method for determining an analyte concentration in a sample using a biosensor, comprising:
    generating at least two analyte responsive output signals from a sample;
    measuring the two analyte responsive output signals from the sample;
    determining at least two initial analyte concentrations from the two analyte responsive output signals;
    determining a first pseudo-reference concentration from the two analyte responsive output signals, the first pseudo-reference concentration being a first substitute for true relative error;
    determining at least two first anchor parameters in response to the first pseudo-reference concentration, the two first anchor parameters compensating for system error, at least one of the two first anchor parameters being a first channel signal-based anchor parameter determined in response to a first normalized output signal and a pseudo-reference signal, the first channel signal-based anchor parameter=$(NR_{OSV1}-NR_{Pseudo})/NR_{Pseudo}$, $NR_{OSV1}$ being a first normalized output signal value and $NR_{Pseudo}$ being a pseudo-reference signal;
    incorporating the two first anchor parameters into at least two first compensation relationships, at least one of the two first compensation relationships including Ach1_comp=Ach1initial/(1+RECh1), Ch1 being channel 1, Ach1_comp being the anchor parameter compensated analyte concentration determined for channel 1, Ach1 initial being the initial analyte concentration determined for channel 1;
    determining at least two first anchor compensated analyte concentrations in response to the two initial analyte concentrations, the two first anchor parameters, and the two first compensation relationships;
    determining a second pseudo-reference concentration by averaging the two first anchor compensated analyte concentrations, the second pseudo-reference concentration being a second substitute for true relative error; and
    reporting the second pseudo-reference concentration as a final compensated analyte concentration of the sample.

2. The method of claim 1, further comprising:
    determining at least two second anchor parameters in response to the second pseudo-reference concentration, the two second anchor parameters compensating for system error;
    incorporating the two second anchor parameters into at least two second compensation relationships;
    determining at least two second anchor compensated analyte concentrations in response to the two initial analyte concentrations, the two second anchor parameters, and the two second compensation relationships;
    determining a third pseudo-reference concentration by averaging the two second anchor compensated analyte concentrations, the third pseudo-reference concentration being a third substitute for true relative error; and
    reporting the third pseudo-reference concentration as the final compensated analyte concentration of the sample.

3. The method of claim 2, further comprising:
    determining at least two third anchor parameters in response to the third pseudo-reference concentration, the one two third anchor parameters compensating for system error;
    incorporating the one two third anchor parameters into at least two third compensation relationships;
    determining at least two third anchor compensated analyte concentrations in response to the two initial analyte concentrations, the two third anchor parameters, and the two third compensation relationships;
    determining a fourth pseudo-reference concentration by averaging the two third anchor compensated analyte concentrations, the fourth pseudo-reference concentration being a fourth substitute for true relative error; and
    reporting the fourth pseudo-reference concentration as the final compensated analyte concentration of the sample.

4. The method of claim 1, wherein the determining of the first pseudo-reference concentration includes comprises averaging the at least two analyte responsive output signals.

5. The method of claim 1, wherein the determining of the first pseudo-reference concentration includes:
    averaging the two analyte responsive output signals; and
    converting an averaged signal of the two analyte responsive output signals into the second pseudo-reference concentration.

6. The method claim 1, wherein the two first anchor parameters include comprises at least one concentration-based anchor parameter.

7. The method of claim 6, further comprising determining the concentration-based anchor parameter by subtracting the first pseudo-reference concentration from one of the two initial analyte concentrations and dividing by the first pseudo-reference concentration.

8. The method of claim 1, wherein the determining of the two first anchor parameters includes comprises:
    determining a second channel signal-based anchor parameter in response to a second normalized output signal value and the pseudo-reference signal.

9. The method of claim 8,
    wherein the second channel signal-based anchor parameter includes a second signal anchor parameter=$(NR_{OSV2}-NR_{Pseudo})/NR_{Pseudo}$, $NR_{OSV2}$ being the second normalized output signal value and $NR_{Pseudo}$ being the pseudo-reference signal value.

10. The method of claim 8, further comprising:
    determining the first normalized output signal value in response to a first analyte responsive output signal and a normalizing relationship, determining the second normalized output signal value in response to a second analyte responsive output signal and the normalizing relationship; and determining the pseudo-reference signal in response to the pseudo-reference concentration and a normalized reference correlation.

11. The method of claim 1, wherein the two first compensation relationships further include:

Ach3_comp=Ach3initial/(1+RECh3), Ch3 being channel 3, Ach3_comp being the anchor parameter compensated analyte concentration determined for channel 3, Ach3initial being the initial analyte concentration determined for channel 3, and RECh3 being the compensation relationship as determined for channel 3.

12. The method of claim 1, wherein the final compensated analyte concentration includes comprises at least one of glycated hemoglobin and glucose, and where the sample including comprises blood.

13. A biosensor system for determining an analyte concentration in a sample, comprising:

a test sensor having a sample interface adjacent to a reservoir formed by a base, where the test sensor is capable of generating at least two analyte responsive output signals from a sample; and a measurement device having a processor connected to a sensor interface, the sensor interface having electrical communication with the sample interface, and the processor having electrical communication with a storage medium;

wherein the processor is capable of measuring the two analyte responsive output signals from the sample;

wherein the processor is capable of determining at least two initial analyte concentrations from the two analyte responsive output signals;

wherein the processor is capable of determining a first pseudo-reference concentration from the two analyte responsive output signals, the first pseudo-reference concentration being a first substitute for true relative error;

wherein the processor is capable of determining at least two first anchor parameters in response to the first pseudo-reference concentration, the two first anchor parameters compensating for system error, at least one of the two first anchor parameters being a first channel signal-based anchor parameter determined in response to a first normalized output signal and a pseudo-reference signal, the first channel signal-based anchor parameter=$(NR_{OSV1}-NR_{Pseudo})/NR_{Pseudo}$, $NR_{OSV1}$ being a first normalized output signal value and $NR_{Pseudo}$ being a pseudo-reference signal;

wherein the processor is capable of incorporating the two first anchor parameters into at least two first compensation relationships, at least one of the two first compensation relationships including Ach1_comp=Ach1initial/(1+RECh1), Ch1 being channel 1, Ach1_comp being the anchor parameter compensated analyte concentration determined for channel 1, Ach1 initial being the initial analyte concentration determined for channel 1;

wherein the processor is capable of determining at least two first anchor compensated analyte concentrations in response to the two initial analyte concentrations, the two first anchor parameters, and the two first compensation relationships;

wherein the processor is capable of determining a second pseudo-reference concentration by averaging the two first anchor compensated analyte concentrations, the second pseudo-reference concentration being a second substitute for true relative error; and wherein the processor is capable of reporting the second pseudo-reference concentration as a final compensated analyte concentration of the sample.

14. The biosensor system of claim 13, further comprising:

wherein the processor is capable of determining at least two second anchor parameters in response to the second pseudo-reference concentration, the two second anchor parameters compensating for system error;

wherein the processor is capable of incorporating the two second anchor parameters into at least two second compensation relationships;

wherein the processor is capable of determining at least two second anchor compensated analyte concentrations in response to the two initial analyte concentrations, the two second anchor parameters, and the two second compensation relationships;

wherein the processor is capable of determining a third pseudo-reference concentration by averaging the two second anchor compensated analyte concentrations, the third pseudo-reference concentration being a third substitute for true relative error; and wherein the processor is capable of reporting the third pseudo-reference concentration as the final compensated analyte concentration of the sample.

15. The biosensor system of claim 14, further comprising:

wherein the processor is capable of determining at least two third anchor parameters in response to the third pseudo-reference concentration, the two third anchor parameters compensating for system error;

wherein the processor is capable of incorporating the two third anchor parameters into at least two third compensation relationships;

wherein the processor is capable of determining at least two third anchor compensated analyte concentrations in response to the two initial analyte concentrations, the two third anchor parameters, and the two third compensation relationships;

wherein the processor is capable of determining a fourth pseudo-reference concentration by averaging the two third anchor compensated analyte concentrations, the fourth pseudo-reference concentration being a fourth substitute for true relative error; and wherein the processor is capable of reporting the fourth pseudo-reference concentration as the final compensated analyte concentration of the sample.

16. The biosensor system of claim 13, wherein the two analyte responsive output signals are independent analyte responsive output signals from the sample.

17. The biosensor system of claim 13, wherein the processor is capable of determining a third pseudo-reference concentration by selecting a sample analyte concentration value as the pseudo-reference concentration, wherein the sample analyte concentration value for multiple analyses is on average closer to an actual analyte concentration of the sample than would be independently determined from the two analyte responsive output signals.

18. The biosensor system of claim 17, wherein the processor is capable of determining a first pseudo-reference concentration by averaging the two analyte responsive output signals.

19. The biosensor system of claim 13, wherein the processor is capable of storing the final compensated analyte compensation in the storage medium.

20. A biosensor system for determining an analyte concentration in a sample, comprising:

a test sensor having a sample interface adjacent to a reservoir formed by a base, where the test sensor is capable of generating at least two analyte responsive output signals from a sample; and a measurement device having a processor connected to a sensor interface, the sensor interface having electrical communication with the sample interface, and the processor having electrical communication with a storage medium;

wherein the processor is capable of measuring the two analyte responsive output signals from the sample;

wherein the processor is capable of determining at least two initial analyte concentrations from the two analyte responsive output signals;

wherein the processor is capable of determining a first pseudo-reference concentration from the two analyte responsive output signals, the first pseudo-reference concentration being a first substitute for true relative error;

wherein the processor is capable of determining at least two first anchor parameters in response to the first pseudo-reference concentration, the two first anchor parameters compensating for system error;

wherein the processor is capable of incorporating the two first anchor parameters into at least two first compensation relationships;

wherein the processor is capable of determining at least two first anchor compensated analyte concentrations in response to the two initial analyte concentrations, the two first anchor parameters, and the two first compensation relationships;

wherein the processor is capable of determining a second pseudo-reference concentration by averaging the two first anchor compensated analyte concentrations, the second pseudo-reference concentration being a second substitute for true relative error;

wherein the processor is capable of determining a third pseudo-reference concentration by selecting a sample analyte concentration value as the pseudo-reference concentration;

wherein the sample analyte concentration value for multiple analyses is on average closer to an actual analyte concentration of the sample than would be independently determined from the two analyte responsive output signals; and wherein the processor is capable of reporting the third pseudo-reference concentration as a final compensated analyte concentration of the sample.

* * * * *